United States Patent
Sävmarker et al.

(10) Patent No.: US 10,898,480 B1
(45) Date of Patent: *Jan. 26, 2021

(54) PHARMACEUTICAL COMPOSITION FOR NASAL DELIVERY

(71) Applicant: Orexo AB, Uppsala (SE)

(72) Inventors: Jonas Sävmarker, Uppsala (SE); Robert Rönn, Uppsala (SE)

(73) Assignee: OREXO AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/939,660

(22) Filed: Jul. 27, 2020

Related U.S. Application Data

(63) Continuation of application No. 16/876,468, filed on May 18, 2020, now Pat. No. 10,729,687, which is a
(Continued)

(51) Int. Cl.
*A61K 9/16* (2006.01)
*A61K 31/70* (2006.01)
(Continued)

(52) U.S. Cl.
CPC .......... *A61K 31/485* (2013.01); *A61K 9/0043* (2013.01); *A61K 9/1652* (2013.01); *A61K 9/1682* (2013.01)

(58) Field of Classification Search
CPC .. A61K 9/0043; A61K 9/1652; A61K 9/1682; A61K 31/485; A61K 31/7016; A61P 25/36
See application file for complete search history.

(56) References Cited

U.S. PATENT DOCUMENTS

| 5,082,669 A | 1/1992 | Shirai et al. |
|---|---|---|
| 6,398,074 B1 | 6/2002 | Bruna et al. |

(Continued)

FOREIGN PATENT DOCUMENTS

| CN | 1640402 | 1/2004 |
|---|---|---|
| CN | 1615867 | 10/2004 |

(Continued)

OTHER PUBLICATIONS

Kurti et al. (Toxicology in Vitro 2012; 26:445-454). (Year: 2012).*
(Continued)

*Primary Examiner* — Ernst V Arnold
(74) *Attorney, Agent, or Firm* — Troutman Pepper Hamilton Sanders LLP (Rochester)

(57) ABSTRACT

According to the invention, there is provided a solid pharmaceutical composition formulation for nasal delivery of an opioid antagonist, comprising a pharmacologically-effective amount of an opioid antagonist and a pharmaceutically-acceptable carrier. The compositions are preferably in the form of a powder produced by spray-drying, which are subsequently loaded into single use nasal applicators. Preferred pharmaceutically-acceptable carriers in this regard include disaccharides (e.g. lactose or trehalose) and dextrins (e.g. cyclodextrins or maltodextrins), preferably spray-dried together in combination. Compositions may further comprise an alkyl saccharide, preferably a sucrose ester, such as sucrose monolaurate. The compositions and applicators may be employed in the treatment of opioid overdose in subjects.

15 Claims, 6 Drawing Sheets

Related U.S. Application Data continuation-in-part of application No. 16/506,023, filed on Jul. 9, 2019, now Pat. No. 10,653,690.

(51) Int. Cl.
  A61P 25/36 (2006.01)
  A61K 31/485 (2006.01)
  A61K 9/00 (2006.01)

(56) References Cited

U.S. PATENT DOCUMENTS

| | | |
|---|---|---|
| 6,938,798 B2 | 9/2005 | Stradella |
| 9,724,713 B2 | 8/2017 | Baillet et al. |
| 9,895,444 B2 | 2/2018 | Maggio |
| 10,653,690 B1 | 5/2020 | Sävmarker et al. |
| 10,729,687 B1 | 8/2020 | Sävmarker et al. |
| 2005/0019411 A1 | 1/2005 | Colombo et al. |
| 2015/0018379 A1 | 1/2015 | Strang et al. |
| 2015/0320695 A1 | 11/2015 | Ryoo et al. |
| 2016/0045474 A1 | 2/2016 | Gandhi et al. |
| 2016/0166503 A1 | 6/2016 | Crystal et al. |
| 2016/0235687 A1 | 8/2016 | Prajapati et al. |
| 2017/0071851 A1 | 3/2017 | Keegan et al. |
| 2017/0319509 A1 | 11/2017 | Canal et al. |
| 2018/0092839 A1 | 4/2018 | Gooberman |
| 2018/0193332 A1 | 7/2018 | Loughlin et al. |
| 2019/0070105 A1 | 3/2019 | Amancha et al. |

FOREIGN PATENT DOCUMENTS

| | | |
|---|---|---|
| CN | 1565451 | 1/2005 |
| CN | 1813739 | 11/2005 |
| CN | 1781479 A | 6/2006 |
| CN | 1939358 A | 4/2007 |
| CN | 104547220 A | 4/2015 |
| EP | 0 657 176 | 6/1995 |
| EP | 2251038 A1 | 11/2010 |
| JP | 2000178184 A | 6/2000 |
| WO | 91/09592 | 7/1991 |
| WO | 00/62757 | 10/2000 |
| WO | 2003/061632 A1 | 7/2003 |
| WO | 2004/054511 A2 | 7/2004 |
| WO | 2005/065652 A1 | 7/2005 |
| WO | 2006/085101 A2 | 8/2006 |
| WO | 2007024123 A1 | 3/2007 |
| WO | 2008/033023 A2 | 3/2008 |
| WO | 2009/040595 A1 | 4/2009 |
| WO | 2009/120735 A1 | 10/2009 |
| WO | 2010/142696 A1 | 12/2010 |
| WO | 2011/036521 A2 | 3/2011 |
| WO | 2015/095644 A1 | 6/2015 |
| WO | WO-2015095389 A1 * | 6/2015 |
| WO | 2016/016431 A1 | 2/2016 |
| WO | 2016/133863 A1 | 8/2016 |
| WO | 2016/161501 A1 | 10/2016 |
| WO | 2017/158439 A1 | 9/2017 |
| WO | 2018/064377 A1 | 4/2018 |
| WO | 2018/064672 A1 | 4/2018 |
| WO | 2018/089709 A1 | 6/2018 |
| WO | 2018/093666 A1 | 6/2018 |
| WO | 2018/148382 A1 | 8/2018 |
| WO | 2019/038756 A1 | 2/2019 |

OTHER PUBLICATIONS

Del Valle, "Cyclodextrins and their Uses: A Review," Process Biochemistry 39:1033-1046 (2004).
Per Gisle Djupesland, "Nasal Drug Delivery Devices: Characteristics and Performance in a Clinical Perspective—A Review," Drug Deliv. and Transl. Res. 3:42-62 (2013).
Fasiolo et al., "Opportunity and Challenges of Nasal Powders: Drug Formulation and Delivery," Eur. J. Pharm. Sci. 113:2-17 (2018).
Florence et al., "The Economic Burden of Prescription Opioid Overdose, Abuse and Dependence in the United States," Med Care, 54(10):901-906 (2016).
Górska et al., "The influence of Trehalose—Maltodextrin and Lactose—Maltodextrin Matrices on Thermal and Sorption Properties of Spray-Dried β-Lactoglobulin—Vitamin D3 Complexes," J. Therm. Anal. Calorim. 112:429-436 (2013).
Hahn & Sucker, "Solid Surfactant Solutions of Active Ingredients in Sugar Esters," Pharm. Res. 6(11):958-960 (1989).
Jüptner et al., "Spray Dried Formulations of Nasal Applications—Challenges and Opportunities in Filling and Drug Delivery," Respiratory Drug Delivery 2:345-348 (2018).
Kürti et al., "The Effect of Sucrose Esters on a Culture Model of the Nasal Barrier," Toxicology in Vitro 26:445-454 (2012).
Li et al., "Non-Ionic Surfactants as Novel Intranasal Absorption Enhancers: In Vitro and In Vivo Characterization," Drug Delivery 23(7):2272-2279 (2016).
Middleton et al., "The Pharmacodynamic and Pharmacokinetic Profile of Intranasal Crushed Buprenorphine and Buprenorphine/Naloxone Tablets in Opioid Abusers," Addiction 106:1460-1473 (2011).
Momin et al., "Investigation into Alternative Sugars as Potential Carriers for Dry Powder Formulation of Budesonide," BioImpacts 1(2):105-111 (2011).
Naini et al., "Physicochemical Stability of Crystalline Sugars and Their Spray-Dried Forms: Dependence upon Relative Humidity and Suitability for Use in Powder Inhalers," Drug Development and Industrial Pharmacy 24(10):895-909 (1998).
Pozzoli et al., "Dry Powder Nasal Drug Delivery: Challenges, Opportunities and a Study of the Commercial Teijin Puvlizer Rhinocort Device and Formulation," Drug Dev. Ind. Pharm. 42(10):1660-1668 (2016).
Pozzoli et al., "Development of a Soluplus Budesonide Freeze-Dried Powder for Nasal Drug Delivery," Drug Dev. Ind. Pharm. 43(9):1510-1518 (2017).
Prekupec et al., "Misuse of Novel Synthetic Opioids: A Deadly New Trend," J. Addic. Med. 11(4):256-265 (2017).
Rudd et al., "Increases in Drug and Opioid-Involved Overdose Deaths—United States, 2010-2015," MMWR 65(50-51):1445-1452 (2016).
Russo et al., "Primary Microparticles and Agglomerates of Morphine for Nasal Insufflation," J. Phar, Sci. 95(12):2553-2561 (2006).
Sacchetti et al., "Caffeine Microparticles for Nasal Administration Obtained by Spray Drying," Int. J. Pharm. 242:335-339 (2002).
Saokham and Loftsson, "γ-Cyclodextrin," Int. J. Pharm. 516:278-292 (2017).
Szüts and Szabó-Révész, "Sucrose Esters as Natural Surfactants in Drug Delivery Systems—A Mini-Review," Int. J. Pharm. 433:1-9 (2012).
Valdés et al., "Physicochemical Characterization and Cytotoxic Studies of Nonionic Surfactant Vesicles using Sucrose Esters as Oral Delivery Systems," Colloids and Surfaces B: Biointerfaces 117:1-6 (2014).
Vengerovich et al., "Analysis of the Efficiency of Microencapsulated Sustained-Release Form of Naloxone on the Experimental Model of Fentanyl Poisoning," Bull. Exp. Biol. Med 163(6):737-741 (2017).
Zhao et al., "Hydroxypropyl-β-Cyclodextrin as Anti-Hygroscopicity Agent Inamorphous Lactose Carriers for Dry Powder Inhalers," Powder Technology 2-11 (2018).
Barnett et al., "Therapeutic Reviews," Journal of Pain and Sumptom Management 47(2):341-352 (2014).
Santosh Thorat, "Formulation and Product Development of Nasal Spray: An Overview," SJAMS 4(8D):2976-2985 (2016).
Oliveira et al., Spray Drying of Food and Herbal Products, Chapter 5 pp. 113-156 (2010).
Piyush Mehta, "Imagine the Superiority of Dry Powder Inhalers from Carrier Engineering," Journal of Drug Delivery vol. 2018 19 Pages (2018).
Dowd et al., "Pharmacology and Therapeutics for Dentistry," p. 319 (2010).

(56) References Cited

OTHER PUBLICATIONS

Amaro et al., "Co-Spray Dried Carbohydrate Microparticles: Crystallisation Delay/Inhibition and Improved Aerosolization Characteristics Through the Incorporation of Hydroxypropylβ-Cyclodextrin with Amorphous Raffinose or Trehalose," Pharm. Res. 32:180-195 (2015).
Written Opinion and International Search Report for PCT/GB2020/051207, dated Nov. 17, 2020.

* cited by examiner

PHARMACEUTICAL COMPOSITION FOR NASAL DELIVERY

This application is a Continuation of U.S. patent application Ser. No. 16/876,468, filed May 18, 2020, which is a Continuation-in-Part of U.S. patent application Ser. No. 16/506,023, filed on Jul. 9, 2019, now U.S. Pat. No. 10,653,690, which are hereby incorporated by reference in their entirety.

This invention relates to new pharmaceutical compositions containing opioid antagonists that are useful in the treatment of inter alia opioid/opiate overdose. The invention also relates to methods of manufacturing such compositions and formulating them into dosage forms, as well as their use in the treatment of opioid/opiate overdose.

PRIOR ART AND BACKGROUND

The listing or discussion of an apparently prior-published document in this specification should not necessarily be taken as an acknowledgement that the document is part of the state of the art or common general knowledge.

Drug addiction is a worldwide problem, of which opioid dependence is a major component. Opioids and opiates are highly addictive. People often start using illegal opioids, such as heroin (diamorphine), for recreational purposes, but this commonly leads to dependency.

That said, a new cohort of opioid-dependent individuals has begun to emerge in the last decade or so, particularly in the US, namely so-called 'white collar' addicts, who have become dependent upon prescription opioids, typically initiated for the treatment of pain.

This occurs because of the increasingly extensive use of medicinal opioids as analgesics, in the treatment of moderate to severe, chronic cancer pain, as well as acute pain (e.g. during recovery from surgery and breakthrough pain). Further, their use is increasing in the management of chronic, non-malignant pain.

People who become addicted to prescription opioids sometimes move on to illicit ('street') drugs, such as heroin. This may be because heroin is cheaper and (relatively speaking) easier to obtain than a prescription opioid.

It was estimated in 2010 that there were 15.5 million opioid-dependent people globally. Prevalence in Australasia, Western Europe, and North America was higher than the global-pooled prevalence. According to the European Monitoring Centre for Drugs and Drug Addiction Report in 2017, there were an estimated 1.3 million high-risk opioid users in Europe in 2016. The opioid crisis has affected the US especially, and this has escalated during recent years.

Thus, opioid dependence is a major health problem and long-term opioid use is connected to a substantially increased risk of premature death from drug overdoses, violence and suicide, as well as various other well publicized health issues, with an increasingly burgeoning socio-economic impact in terms of cost of healthcare, lost productivity, addiction treatment, and criminal activity (see Florence et al, *Med. Care.,* 54, 901 (2016)).

Opioid addicts typically feed their addiction by direct purchase of opioids 'on the street', in the form of opioid-based powders (such as heroin). Heroin is usually mixed (or 'cut') with additives prior to sale by drug dealers, the amount and identity of which is almost always unknown to the abuser. Furthermore, there is an increasing number of addicts being sold, and abusing, more potent opioids intended for the treatment of e.g. pain, such as fentanyl and its analogues (see e.g. Prekupec et al, *J. Addict. Med.,* 11, 256-265 (2017)).

Even without these additional issues, opioids are extremely dangerous drugs if not delivered under medical supervision. As there are no quality controls on illicit drugs that are sold, particularly in relation to the purity and strength issues discussed above, the whole process is something of a 'lottery', which serves to add to the danger and likelihood of overdose.

Overdose of opioids leads to depressed heart rate and breathing, leading to hypoxia. Hypoxia not only leads to short- and long-term effects on the central nervous system, including coma and permanent brain damage, but often leads to fatality. Overdoses of opioids, particularly heroin are very common. In 2015, drug overdoses accounted for 52,404 US deaths, of which 33,091 (63.1%) involved an opioid (see Rudd et al, *MMWR,* 65, 1445 (2016)). It is not unheard of for people to overdose the very first time they use heroin.

A subject that has overdosed on an opioid requires urgent medical attention. The only medicines that can be employed to treat opioid overdoses effectively are opioid receptor antagonists, which act by binding to opioid receptors, displacing opioid agonists (like heroin) without eliciting opioid effects of their own, whether intended (e.g. euphoria) or unintended and/or potentially dangerous (including respiratory depression). Emergency administration of opioid antagonists can reduce (sometimes completely) the degree of opioid intoxication and, in essence, 'reverse' an opioid overdose.

Opioid antagonists are administered as intravenous solutions in Accident and Emergency departments hospitals by medically-qualified staff. However, outside of the hospital environment, there are relatively few treatments available for the treatment of an opioid overdose (or a suspected overdose).

Two such treatments that are available commercially comprise the opioid antagonist, naloxone, delivered in the form of a single dose either as a liquid nasal spray (Narcan®; which is sprayed directly into one nostril), or as an auto-injector (Evzio®; which delivers drug by injection into the muscle or under the skin). These treatments are often employed by first responders (i.e. non-medically qualified personnel, such as ambulance crews, paramedics, police officers, family members, friends or other caregivers), buying time until more qualified medical assistance is available.

These products are undoubtedly effective in helping to save lives. Naloxone and other opioid antagonists are highly water-soluble drugs, which enables the dissolution of an effective dose of e.g. naloxone in a small quantity of liquid (100 µL) in a product like Narcan to treat opioid overdose. This enables it to act quickly in an emergency situation.

However, in about one third of cases, Narcan is known to require two or more doses in order to effect reversal of the overdose. Furthermore, Narcan has the disadvantage that it should not be allowed to freeze (otherwise it cannot be dispensed). This is a problem in cold climates, for example if the product is left inside a first responder's vehicle overnight.

Evzio, on the other hand, is a parenteral product that requires a needle, presenting significant difficulties and/or problems for some first responders in what is an urgent situation.

Because of the huge increase in overdose deaths from opioid misuse, there is considerable demand for opioid overdose prevention medications, and also a clear clinical need for alternative and/or improved medications, in terms of their strength, onset and duration of action, as well as reproducibility and reliability in an emergency situation, which treating an opioid overdose undoubtedly is.

In addition to the commercial product, Narcan, liquid intranasal sprays are also disclosed in international patent application WO 2018/064672 and US patent applications US 2018/0092839A and US 2019/0070105A.

Dry powder formulations comprising opioid antagonists that may be administered by inhalation or intranasally are known from inter alia international patent applications WO 2010/142696 and WO 2019/038756, and US patent application US 2018/0092839A.

Russo et al (*J. Pharm. Sci.*, 95, 2253 (2006)) discloses spray-drying the opioid analgesic compound, morphine, with numerous excipients. Spray-dried formulations are also disclosed in Vengerovich et al., *Bulletin of Experimental Biology and Medicine*, 163, 737 (2017), where it was attempted to microencapsulate naloxone in various substances, including 2-hydroxypropyl-β-cyclodextrin, with a view to developing sustained-release preparations based on polymeric carriers for emergency care.

Sugar esters are a class of natural and biodegradable non-ionic surfactants consisting of a hydrophilic sugar 'head group' esterified with fatty acids. The properties of sugar esters depend on the nature of the sugar and fatty acids used, and the degree of esterification of the sugar. They are made from natural products, sugar and edible fats, are tasteless, odourless and biodegradable, and are relatively nontoxic with a recommended acceptable daily intake of up to 30 mg/kg (joint FAO/WHO Expert Committee on Food Additives (JECFA)). Sugar esters, and in particular sucrose esters, are widely used in the food and cosmetics industries but, thus far, are relatively underutilised in pharmaceutical formulations (see, for example, the review article by Szüts and Szabó-Révész in *Int. J. Pharm.*, 433, 1 (2012)).

Sucrose esters are known to be excellent oil-in-water-type emulsifiers. For example, emulsion-based compositions comprising sucrose esters are described in international patent application WO 2005/065652. See also international patent application WO 2003/061632.

Sucrose esters have also been employed to improve the bioavailability of poorly water-soluble drugs, such as ciclosporin in perorally administered dosage forms (see Hahn and Sucker, *Pharm. Res.*, 6, 958 (1989)). (It is to be noted that naloxone and other opioid antagonists are highly water-soluble.)

Other peroral dosage forms comprising sucrose esters are described in inter alia international patent application WO 2016/016431.

International patent applications WO 2015/095389 and WO 2018/089709, and U.S. Pat. No. 9,895,444, also disclose that related compounds, sugar ethers and in particular alkyl glycosides, can increase the bioavailability of opioid compounds in liquid nasal sprays. Sucrose esters are also mentioned in these documents. Similar drug delivery vehicles are disclosed in US patent application US 2016/0045474. Furthermore, Kürti et al investigated the effect of sucrose esters on epithelial permeability in a culture model (see Toxicology in Vitro, 26, 445 (2012)), and Li et al investigated the effect of various surfactants, including sucrose laurate, in in vivo absorption studies in rats, using sumatriptan as a model drug substance (see *Drug Delivery*, 23, 2272 (2016)).

However, to the applicant's knowledge, there is no reported use of sucrose esters in solid (e.g. powder) formulations intended for intranasal delivery.

We have now unexpectedly found that it is possible to formulate opioid antagonists in the form of dry powder compositions, that provide for a surprising and substantial improvement in bioavailability of opioid antagonist, as well as, even more surprisingly, an increase in the speed of absorption of opioid antagonist, compared to commercially-available products. In particular, we have found that compositions that are produced by a process of spray-drying with a specific combination of carrier materials as disclosed hereinafter, and/or similar dry powder compositions that comprise an alkyl saccharide, such as a sucrose ester, are capable of giving rise to these unexpected effects.

DISCLOSURE OF THE INVENTION

Figures 1, 2:
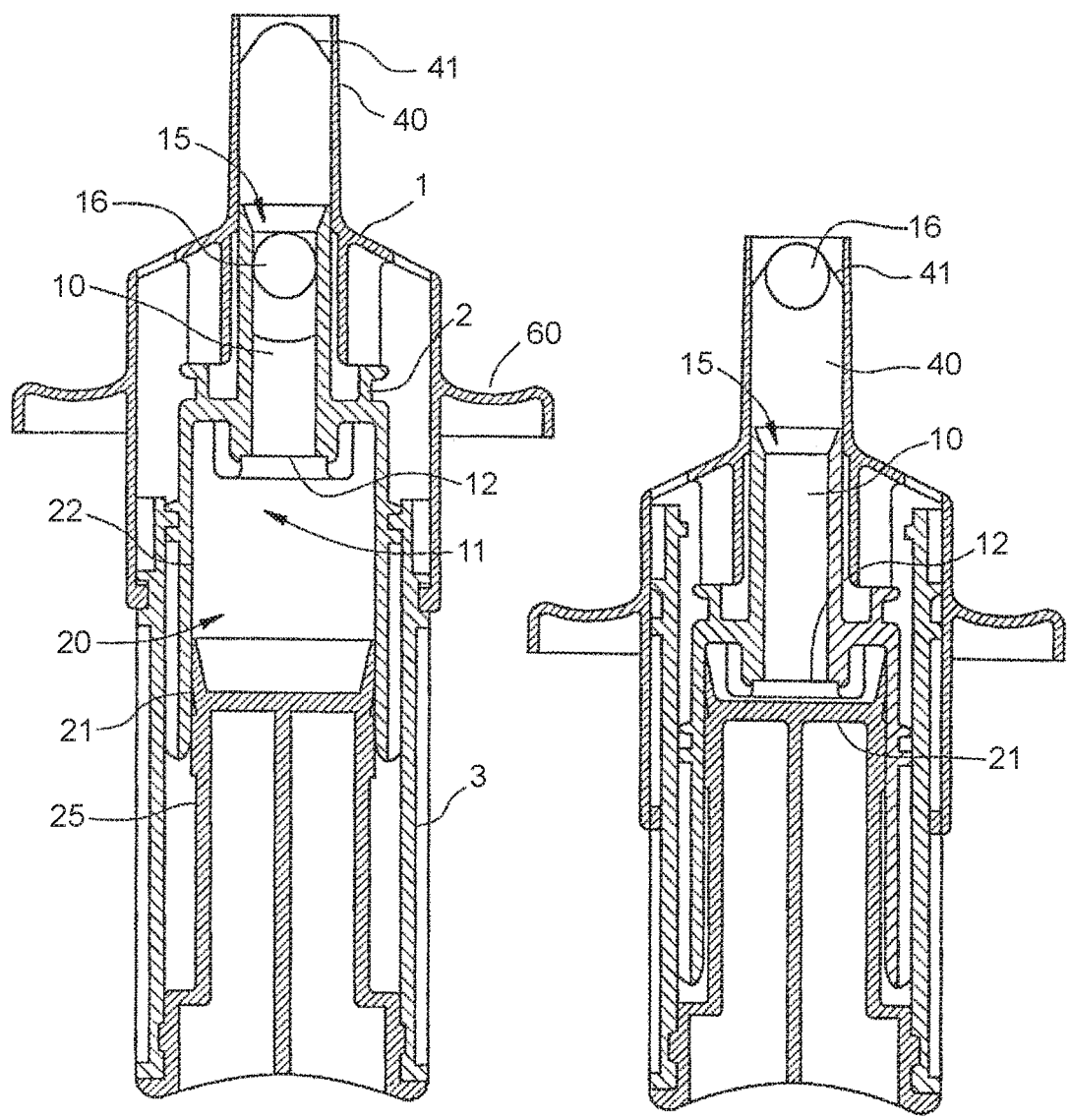
FIG. 1 is a diagrammatic sectional view of a first suitable applicator based on the disclosure of U.S. Pat. No. 6,398,074, which is incorporated herein by reference. As shown, the applicator is configured before actuation.
FIG. 2 is a sectional view of the applicator shown in FIG. 1, but after actuation.
Figure 3:
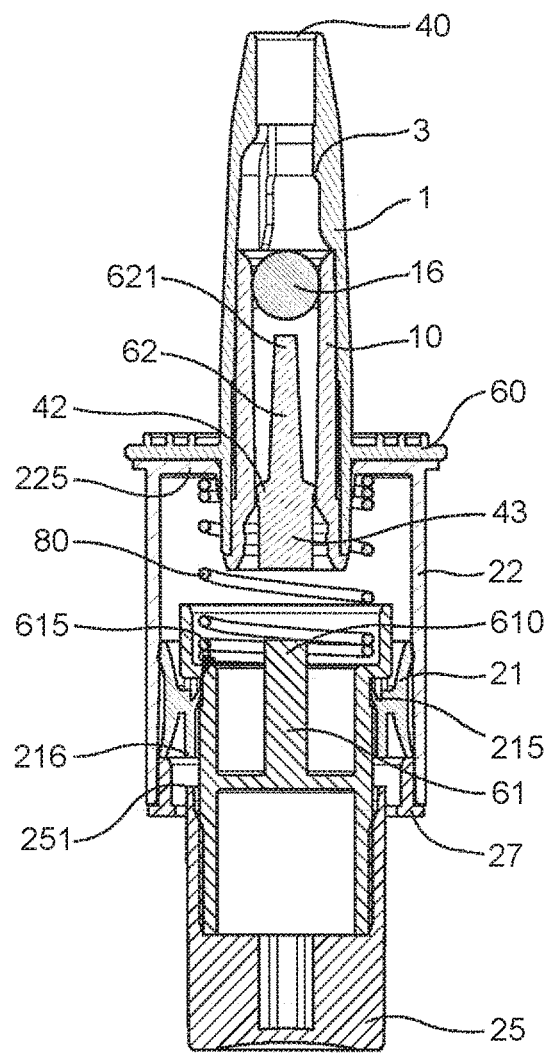
FIG. 3 is a diagrammatic sectional view of a second suitable applicator based on the disclosure of U.S. Pat. No. 9,724,713, which is incorporated herein by reference. As shown, the applicator is configured in the rest position.
Figure 4:
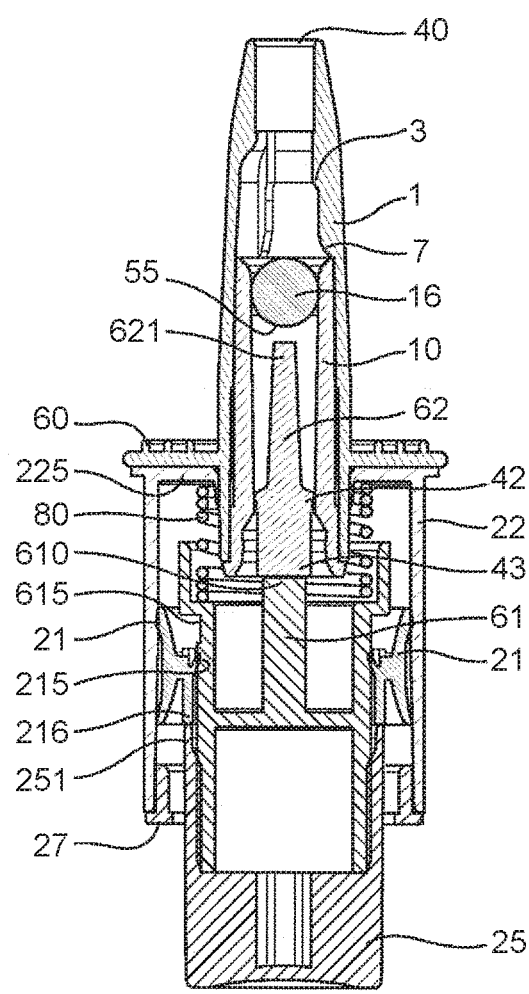
FIG. 4 is a sectional view of the applicator shown in FIG. 3, but now configured in the actuation position.
Figure 5:
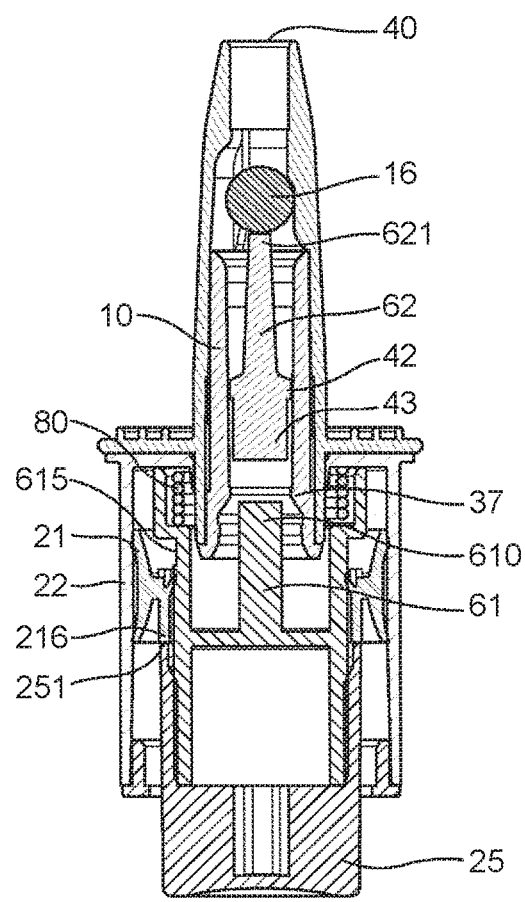
FIG. 5 is a sectional view of the applicator shown in FIG. 3, but now configured in the dispensing position.
Figure 6:
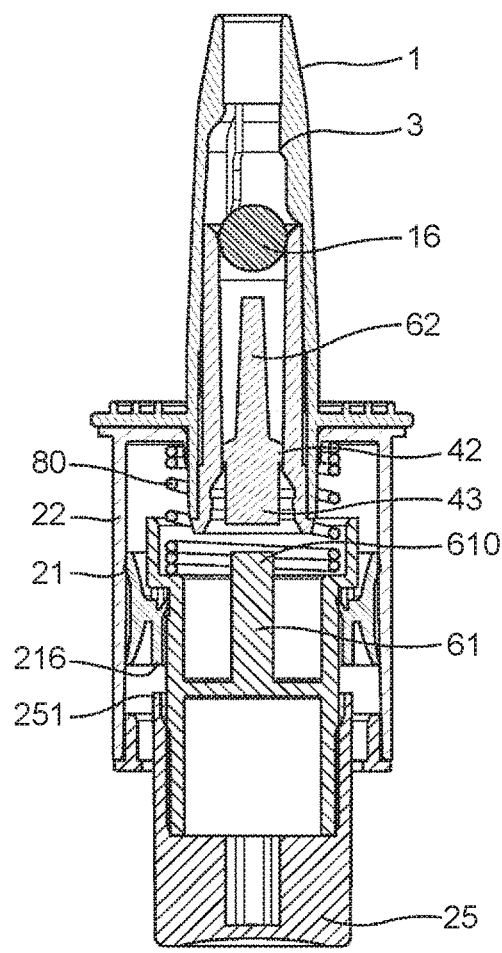
FIG. 6 is a sectional view of the applicator shown in FIG. 3, but now configured during return of the air expeller towards its rest position.

According to a first aspect of the invention, there is provided a solid pharmaceutical formulation/composition that is suitable for nasal delivery of an opioid antagonist, comprising a pharmacologically-effective amount of an opioid antagonist, and a pharmaceutically-acceptable carrier material.

According to a second aspect of the invention, there is provided a solid pharmaceutical formulation/composition in the form of a powder that is suitable for nasal delivery of an opioid antagonist, comprising a pharmacologically-effective amount of an opioid antagonist, optionally an alkyl saccharide, and a pharmaceutically-acceptable carrier material.

Preferably, the powder is produced by a process of spray-drying. According to a third aspect of the invention, there is provided a solid pharmaceutical formulation/composition in the form of a spray-dried powder that is suitable for nasal delivery of an opioid antagonist, comprising a pharmacologically-effective amount of an opioid antagonist and a pharmaceutically-acceptable carrier material, more preferably a carrier material that comprises a combination of at least two pharmaceutically-acceptable carrier materials, at least one of which carrier materials is a disaccharide and at least one of which carrier materials is a dextrin.

Compositions of the first, second and third aspects of the invention are referred to hereinafter together as 'the compositions of the invention'.

The term 'solid' will be well understood by those skilled in the art to include any form of matter that retains its shape and density when not confined, and/or in which molecules are generally compressed as tightly as the repulsive forces among them will allow.

Opioid antagonists that may be employed in compositions of the invention include any compound that has little to no opioid activity, but is capable of displacement of an opioid agonist from an opioid receptor, so reversing or preventing the pharmacological effects of an opioid agonist, whether such effects are intended (euphoria, sedation and/or reduction in cravings), or unintended (unconsciousness, depressed heart rate, depressed lung function, hypoxia, etc.). In this respect, the term 'opioid agonists' include exogenous opioid receptor ligands (i.e. those mentioned hereinbefore) and endogenous opioid receptor ligands (e.g. endorphins).

Opioid antagonists thus include naloxone, nalmefene and naltrexone, or pharmacologically-acceptable salts thereof. Preferred salts of these compounds include hydrochloride salts. Naloxone and nalmefene (and salts of either) are particularly preferred.

In the context of the present invention, the term 'opioid antagonists' may also include active pharmaceutical ingredients that are known to be partial antagonists of opioid receptors, such as buprenorphine. Buprenorphine may be termed as a 'partial antagonist of opioid receptors' because it is a partial agonist at the μ-opioid receptor. It has high binding affinity, and competes with other agonists, such as methadone, heroin and morphine, at the μ-opioid receptor. Opioid agonist effects of buprenorphine are less than the maximal effects of other, 'full' opioid agonists, such as morphine, and are limited by a 'ceiling' effect. The drug thus produces a lower degree of physical dependence than other opioid agonists, such as heroin, morphine or methadone and is therefore used in substitution therapy. There is a reduced risk of overdose and reduced recreational value in opioid-tolerant subjects. Buprenorphine has been listed on the WHO's List of Essential Medicines for the treatment of opioid dependence. Displacement of full agonists may make buprenorphine useful in the context of the invention by being capable of reversing an opioid overdose, with a lower degree of precipitated withdrawal compared with full antagonists.

The amount of opioid antagonist that is employed in a composition of the invention must be sufficient so as to antagonize the effect of the opioid receptor agonists (whether exogenous and/or endogenous), precipitate withdrawal symptoms and/or effect reversal of the pharmacological effects mentioned above. Pharmacologically-appropriate amounts of opioid antagonist (or salt thereof) may be determined by the skilled person and may vary with the type and severity of the condition that is to be treated, and what will be most suitable for an individual patient. This is also likely to vary with the nature of the formulation, as well as the route of administration, the type and severity of the condition that is to be treated, as well as the age, weight, sex, renal function, hepatic function and response of the particular patient to be treated.

The total amount of opioid antagonist that may be employed in a composition of the invention will depend on the nature of the active compound that is included, but may be in the range of from about 0.1%, such as about 1%, for example about 2% up to about 95%. For example, the amount of opioid antagonist may be from about 5%, such as about 10% (e.g. about 20%) to about 95%, such as about 75%, for example about 50%, e.g. about 40%, by weight based upon the total weight of the composition.

Appropriate doses of opioid antagonist (calculated as the free acid/base) per unit dosage are in the range of about 1 mg to about 60 mg (e.g. about 40 mg), such as between about 2 mg and about 30 mg (e.g. about 20 mg, such as about 10 mg), depending on the opioid antagonist that is employed.

Appropriate doses of naloxone (calculated as the free base) are in the range of about 1 mg to about 20 mg (e.g. about 15 mg), such as between about 1.5 mg and about 10 mg, and may thus be about 1.8 mg, about 5.4 mg, about 9.0 mg (e.g. about 10.8 mg), more preferably about 3.6 mg and especially about 7.2 mg.

Appropriate doses of nalmefene (calculated as the free base) per unit dosage may be about 0.5 to about 10 mg, more preferably about 1 mg to about 6 mg, including about 1.5 mg and, especially, about 3.0 mg.

Appropriate doses of naltrexone (calculated as the free base) per unit dosage form may be about 1 mg to about 20 mg (e.g. about 15 mg), more preferably about 1.5 mg to about 10 mg.

In relation to either of the aforementioned aspects of the invention, appropriate pharmaceutically-acceptable carrier materials that may be employed in compositions include any such relevant material that is suitable (and/or approved) for pharmaceutical use and/or for intranasal delivery, and is capable of maintaining its physical and/or chemical integrity, and/or does not affect the physical and/or chemical integrity of the opioid antagonist and/or any other ingredients that may be present in the composition (such as alkyl saccharide), in the solid state, under normal storage conditions.

The phrase 'maintaining physical and chemical integrity' essentially means chemical stability and solid state stability.

By 'chemical stability', we include that any composition of the invention may be stored in isolated solid form, or when loaded into a nasal applicator or a reservoir therefor (with or without appropriate pharmaceutical packaging), under normal storage conditions, with an insignificant degree of chemical degradation or decomposition.

By 'solid state stability', we include that any composition of the invention may be stored in an isolated solid form, or when loaded into a nasal applicator or a reservoir therefor (with or without appropriate pharmaceutical packaging), under normal storage conditions, with an insignificant degree of solid state transformation (e.g. crystallisation, recrystallisation, loss of crystallinity, solid state phase transition (e.g. between a glassy or a rubbery state, or to an agglomerated form)), hydration, dehydration, solvatisation or desolvatisation.

Examples of 'normal storage conditions' for compositions of the invention, whether loaded into applicators, devices, drug reservoirs (such as canisters or containers) or otherwise, include temperatures of between about −50° C. and about +80° C. (preferably between about −25° C. and about +75° C., such as about 50° C.), and/or pressures of between about 0.1 and about 2 bars (preferably atmospheric pressure), and/or exposure to about 460 lux of UV/visible light, and/or relative humidities of between about 5 and about 95% (preferably about 10 to about 40%), for prolonged periods (i.e. greater than or equal to about twelve, such as about six months).

Under such conditions, compositions of the invention may be found to be less than about 15%, more preferably less than about 10%, and especially less than about 5%, chemically degraded/decomposed, and/or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

Such chemical and, particularly, physical stability is of critical importance in a solid state formulation, such as a powder, that is to be employed in the treatment of e.g. an opioid overdose.

It is well known that significant difficulties may be experienced in attempting to obtain both chemically- and physically-stable solid compositions, such as powders. In the present case, if the physical form of a composition of the invention changes under normal storage conditions (e.g. from a free flowing powder to an agglomerated mass that is difficult to discharge), it will likely lead to non-reproducibility of dose of opioid antagonist when dispensing a composition (or even the complete inability to dispense it) from, or via, a nasal applicator, which will put the subject's life at significant risk.

For certain compositions of the invention (e.g. powders), exposure to atmospheric water may result in compositions that are less solid-state stable. For example, exposure to certain (e.g. higher) relative humidities may affect the physical form of the composition, for example by deliquescence, and/or by lowering glass transition temperatures of compositions, and/or individual components of the compositions, such as carrier materials, or in another way.

Accordingly, compositions of the invention, and nasal applicators including them, are preferably packaged within containers that substantially prevent the ingress of atmospheric water under the normal storage conditions hereinbefore defined. Such containers may include packaging materials such as heat-sealed aluminium pouches and/or thermoformed plastics.

When the composition includes an alkyl saccharide, appropriate pharmaceutically-acceptable solid carrier materials thus include cellulose and its derivatives, such as sodium carboxymethyl cellulose, ethyl cellulose, cellulose acetate, hydroxypropylmethyl cellulose (hypromellose, HPMC), hydroxyethyl cellulose (HEC), hydroxypropyl cellulose (HPC), methyl cellulose (MC), ethyl hydroxyethyl cellulose, carboxymethyl cellulose (CMC), modified cellulose gum, microcrystalline cellulose and sodium carboxymethyl cellulose; starches, such as rice starch, tapioca starch, wheat starch and, more particularly, corn starch and potato starch; starch derivatives, such as pregelatinized starch, carboxymethyl starch, as well as moderately cross-linked starch, modified starch and sodium starch glycolate; polysaccharides, including dextrins, such as dextrin, cyclodextrins and linear or branched dextrins, such as maltodextrins; powdered tragacanth; malt; gelatin; talc; waxy excipients, such as cocoa butter and suppository waxes; polyols, such as solid polyethylene glycols; sugars, sugar alcohols and saccharides, such as mannitol, maltitol, xylitol, sorbitol, lactose, glucose, galactose, sucrose, sucralose, trehalose, maltose, isomalt and dextrose; acrylic polymers, such as carbomer and its derivatives; polyvinylpyrrolidone (povidone, PVP); crosslinked polyvinylpyrrolidone; polyethylene oxide (PEO); chitosan (poly-(D-glucosamine)); natural polymers such as gelatin, sodium alginate, pectin; scleroglucan; xanthan gum; guar gum; poly co-(methylvinyl ether/maleic anhydride); and croscarmellose (e.g. croscarmellose sodium). Hypromellose acetate succinate (HPMCAS), copovidone and polyvinyl alcohol (PVA, or PVOH) may also be mentioned. Mixtures of any of the foregoing may be employed.

Compositions according to the first aspect of the invention may thus be compressed into a single unit dosage form, granulated into a pellet or a pill, but are preferably provided in the form of a dry, free-flowing powder. Compositions of the second and third aspects of the invention are provided in the form of a dry, free-flowing powder. In the context of any aspect of the invention, by 'dry' we include essentially free of water and other liquid solvents, which includes that there is less than about 10%, such as less than about 5%, more preferably about 3%, such as less than about 2%, e.g. less than about 1% of the formulation is a liquid, such as water.

Compositions of the invention may thus be administered in the form of a plurality of particles, which particles may individually and/or collectively consist of, and/or comprise, compositions of the invention. Compositions of the invention may be prepared in a form of a simple powder mixtures, powder microspheres, coated powder microspheres, a lyophilised liposomal dispersion, or a combination thereof.

Whether in the form of a powder or otherwise, amounts of carrier material(s) that may be employed in compositions of the invention are typically in the range of about 5% to about 99.9%, including up to about 99% (e.g. up to about 95% or about 90%), such as about 10% (e.g. about 25%, including about 35%) to about 85%, including about 50% to about 75%, by weight, based upon the total weight of the composition.

Furthermore, whether in the form of a powder or otherwise, compositions of the invention may be prepared by standard techniques, and using standard equipment, known to the skilled person. In this respect, the compositions of the invention may be combined with conventional pharmaceutical additives and/or excipients used in the art for relevant preparations, and incorporated into various kinds of pharmaceutical preparations using standard techniques (see, for example, Lachman et al, "*The Theory and Practice of Industrial Pharmacy*", Lea & Febiger, $3^{rd}$ edition (1986); "*Remington: The Science and Practice of Pharmacy*", Troy (ed.), University of the Sciences in Philadelphia, $21^{st}$ edition (2006); and/or "*Aulton's Pharmaceutics: The Design and Manufacture of Medicines*", Aulton and Taylor (eds.), Elsevier, $4^{th}$ edition, 2013).

Dry powders may be prepared by mixing the opioid antagonist along with the pharmaceutically-acceptable carrier material and, if present, the alkyl saccharide, and any other ingredients that may be included. Appropriate techniques that may be employed include simple dry mixing, granulation (including dry granulation, wet granulation, melt granulation, thermoplastic pelletising, spray granulation), extrusion/spheronisation or freeze-drying.

Dry granulation techniques are also well known to those skilled in the art and include any technique in which primary powder particles are aggregated under high pressure, including slugging and roller compaction, for example as described hereinafter.

Wet granulation techniques are well known to those skilled in the art and include any technique involving the massing of a mix of dry primary powder particles using a granulating fluid, which fluid comprises a volatile, inert solvent, such as water, ethanol or isopropanol, either alone or in combination, and optionally in the presence of a binder or binding agent. The technique may involve forcing a wet mass through a sieve to produce wet granules which are then dried, preferably to a loss on drying of less than about 3% by weight.

Melt granulation will be known by those skilled in the art to include any technique in which granules are obtained through the addition of a molten binder, or a solid binder which melts during the process (which binder materials may comprise the pharmaceutically acceptable carrier material). After granulation, the binder solidifies at room temperature. Thermoplastic pelletising will be known to be similar to melt granulation, but in which plastic properties of the binder are employed. In both processes, the agglomerates (granules) obtained comprise a matrix structure.

Extrusion/spheronisation will be well known to those skilled in the art to include any process involving the dry mixing of ingredients, wet massing along with a binder, extruding, spheronising the extrudate into spheroids of uniform size, and drying.

Spray granulation will be known by those skilled in the art to include any technique involving the drying of liquids (solutions, suspensions, melts) while simultaneously building up granulates in a fluid bed. The term thus includes processes in which foreign seeds (germs) are provided upon which granules are built up, as well as those in which inherent seeds (germs) form in the fluid bed due to abrasion and/or fracture, in addition to any spray coating granulation technique generally. The sprayed liquid coats the germs and assists further agglomeration of particles. It is then dried to form granules in the form of a matrix.

The term 'freeze drying' includes lyophilisation or cryo-desiccation, and any low temperature desolvatization (e.g. dehydration) process, in which product is frozen, pressure is lowered, and the frozen solvent (e.g. water) is removed by sublimation.

However, we prefer that compositions of the invention are prepared by a process of spray-drying.

Spray-drying will be understood by the skilled person to include any method of producing a dry powder from a liquid, including a solution or a suspension (including a slurry) that involves rapid drying using hot gas to convert a stream of liquid into vaporized solvent and particles of solid, which solid particles comprise the solute that was previously dissolved in a solution, and/or particles that were previously suspended in the evaporated liquid.

Appropriate spray-drying equipment includes some form of atomization means, such as a spray nozzle, which disperses the liquid into a spray with a relatively uniform droplet size. Such means may include any means that is capable of producing a dry, free-flowing powder, and may include high pressure swirl nozzles, rotary disks and/or atomizer wheels, high pressure single fluid nozzles, two-fluid nozzles and/or ultrasonic nozzles.

The spray-dryer may be a single effect or a multiple effect spray-dryer, and may comprise an integrated and/or an external vibrating fluidized bed, a particle separator, and/or a collection means which may be a drum or a cyclone.

Spray-drying may be employed to produce compositions of the invention in the form of powders and, in doing so, encapsulate substances in a carrier material, or produce an amorphous composite of active ingredient, carrier materials and other ingredients.

In this respect, compositions of the invention in the form of powders, particularly if produced by spray-drying, may be considered to comprise a plurality of particles, which particles are themselves 'mono-particulate' in their nature. By 'mono-particulate', we include that the particles comprise a homogeneous or a heterogeneous mixture, in which active ingredients are encapsulated in an amorphous state within carrier materials in the presence of other ingredients (e.g. an amorphous composite of those things). In this respect, such compositions of the invention do not comprise mixtures of two or more discrete, separate particles of different ingredients in the form of a mixture, such as an ordered, or interactive, mixture of smaller particles of active ingredients associated with larger, but separate and chemically distinct, particles of carrier substances, as is often the case for inhaled drug delivery compositions (see, for example Mehta, *J. Drug Delivery*, Art. ID 5635010, 1-19 (2018)).

Spray-dried compositions of the invention are thus preferably amorphous in their nature, which includes wholly amorphous and/or predominantly amorphous (for example more than about 50% by weight, such as more than about 75% by weight, including more than about 80% by weight, such as more than about 90% by weight, or 95% by weight, including more than about 99% by weight amorphous), and may give rise to pharmaceutical products that show excellent shelf-life, in terms of both physical and chemical stability, when stored under normal storage conditions, as hereinbefore defined.

According to a further aspect of the invention, there is provided a process for the manufacturing of a composition of the invention (in the form of a dry powder), wherein said process comprises the steps of:
  i) mixing together the opioid antagonist, the alkyl saccharide (if present) and the pharmaceutically-acceptable carrier material, in an appropriate volatile solvent,
  ii) spray-drying the mixture from step i) to form a spray-dried plurality of particles.

Preferred volatile solvents include water, or organic solvents, such as lower alkyl alcohols (e.g. ethanol), haloalkanes. Other solvents that may be mentioned include hydrocarbons (e.g. $C_{5-10}$ alkanes), dimethylformamide, dimethylsulfoxide, ethyl acetate, acetone, etc. Mixtures of any of the foregoing solvents may be employed.

We prefer that mixing together the opioid antagonist, the alkyl saccharide (if present) and the pharmaceutically-acceptable carrier material with the solvent results in a solution that can be spray-dried.

Particularly preferred pharmaceutically-acceptable carrier materials that may be employed to produce spray-dried compositions of the invention (whether according to the first, the second or the third aspect of the invention), and which possess the desirable characteristics mentioned herein, include saccharides, more preferably disaccharides, such as maltitol, trehalose, sucralose, sucrose, isomalt, maltose and, particularly, lactose (including β-D-lactose and α-D-lactose, especially α-D-lactose monohydrate); and/or polymers, including any polymeric materials mentioned hereinbefore as appropriate carrier materials (such as sodium carboxymethyl cellulose, sodium starch glycolate, polyvinylpyrrolidone and, particularly, hydroxypropylmethyl cellulose, and the like) and, particularly, polysaccharides, such as dextrins, including cyclodextrins (e.g. α-, β- and γ-cyclodextrins and derivatives thereof, such as, 2-hydroxypropyl-γ-cyclodextrin, sulfobutylether β-cyclodextrin sodium salt, randomly methylated β-cyclodextrin, branched β-cyclodextrin and the like and, particularly, 2-hydroxypropyl-β-cyclodextrin); and linear or branched dextrins, such as maltodextrins, which are classified by DE (dextrose equivalent), which can be between 3 and 20 (the higher the DE value, the shorter the glucose chains), especially maltodextrin with a DE of between 6 and 15, such as 8 and 12.

Also included within the scope of the invention are combinations of two or more of the above-mentioned preferred materials.

It is preferred that a carrier material, whether a single carrier material or a combination of two or more carrier materials, is capable of giving rise to a spray-dried composition of the invention in the form of a powder, wherein the composition possesses a glass transition temperature (Tg) that:

(a) enables its production as a hard and/or brittle, 'glassy', amorphous, powdered physical form, that can be easily loaded into a nasal applicator, or a drug reservoir and/or container within, or adjunct to, such an applicator, as described herein; and (b) is high enough that, after such an applicator or reservoir is packaged as described herein, and thereafter subjected to a high external temperature (e.g. up to about 50° C. to about 80° C.), it remains in that glassy state, rather than being transformed into a more viscous or rubbery state, and/or a crystalline state.

Such extreme external temperatures are often experienced inside vehicles (e.g. of first responders) in warm and/or sunny climates, which vehicles will frequently be parked for extended periods of time in full sun, where the resultant heat gain can be enormous. If the Tg of a composition of the invention is low, the composition may transform after exposure to such high temperatures to such a viscous/rubbery state, this will give rise to inefficient discharging of the composition from the applicator or reservoir (and so too the dose of opioid antagonist) once the applicator is actuated.

In this respect, we prefer that the lowest measurable Tg of a composition of the invention is at least about 40° C., such as at least about 50° C., such as at least about 55° C., including at least about 60° C., when measured at a relative humidity of up to about 35%, such as up to about 30%, including up to about 25% (e.g. up to about 20%, such as less than about 15%, e.g. less than about 10%). By 'lowest measurable Tg', we include that the composition of the invention may comprise particles that are heterogenous in their nature. In particular, if more than one carrier material is employed, particles may comprise discrete regions of carrier materials, or composite mixtures thereof, that may possess individual and separate Tg values. It will be clear to the skilled person that the value of the lowest measurable Tg has a strong impact on the physical stability of the composition.

When the carrier material comprises a combination of one or more disaccharide (as hereinbefore defined) and one or more polymeric ingredients (as hereinbefore defined, but particularly so when the polymer is a dextrin) relative amounts of those ingredients in the combination can be tailored to ensure the required level of physical and/or chemical stability of active ingredient whilst, at the same time, not lowering the Tg of the composition of the invention in such a manner that it affects its physical stability. We have found that a ratio of between about 50:1 to about 1:50 of disaccharide:polymer (e.g. dextrin) by weight, based on the total weight of the composition, may work depending on the active ingredient that is employed. Preferred ratios are in the range of about 10:1 to about 1:40 (including up to about 1:30 or up to about 1:20), for example between about 2:1 and about 1:10, more preferably about 1:1 to about 1:8 of disaccharide:polymer (e.g. dextrin) by weight, based on the total weight of the composition.

In particular, and as described hereinafter, we have found that compositions of the invention, when fabricated by spray-drying and:

(i) employing a disaccharide as a carrier material give rise to vastly improved chemical stability of the opioid antagonist when compared to monosaccharides, such as mannitol. This is surprising, because mannitol has been used previously in physical mixtures together with opioid antagonists, such as naloxone, with no stability issues whatsoever;

(ii) employing a dextrin, such as cyclodextrin or maltodextrin, as a carrier material provide for significantly improved physical stability when compared to other carrier materials.

(iii) However, employing such a dextrin gave rise to an unexpected chemical instability of the opioid antagonist;

(iv) which chemical instability could be solved by spray-drying the dextrin along with a disaccharide.

A particularly preferred combination of carrier materials thus includes a disaccharide, and especially trehalose and, more preferably, a lactose, such as α-D-lactose monohydrate, and a dextrin, and especially a cyclodextrin, such as 2-hydroxypropyl-β-cyclodextrin, or a maltodextrin, such as maltodextrin 12DE. We have found that such a combination of carrier materials can be spray-dried together along with an opioid antagonist and an alkyl saccharide in appropriate proportions to produce a composition of the invention that possesses both the desired physical and chemical stability under normal storage conditions, as hereinbefore defined.

We have found that an amount of between about 5% (particularly about 10%) and about 30%, such as between about 15% and about 25%, e.g. between about 17% and about 24%, by weight based on the total weight of the composition, of disaccharide provides for the required level of chemical stability of opioid antagonist, such as naloxone, whilst at the same time not lowering the Tg of the composition of the invention in such a manner that it affects physical stability. Appropriate amounts of dextrin are accordingly in the range of about 30% up to about 90%, such as up to about 85%, including up to about 80%, and especially up to about 75%, such as between about 40% and about 70%, e.g. between about 43% and 67%, by weight based on the total weight of the composition.

As described hereinafter, compositions of the invention have been found to exhibit surprisingly good bioavailability, and highly surprisingly more rapid absorption, which likely will result in a more rapid onset of action, compared to relevant reference products (e.g., in the case of naloxone, Narcan nasal spray).

This is highly unexpected for several reasons, including that:

(a) unlike compositions of the invention, which are solids, in existing products, such as Narcan, opioid antagonist (in that case naloxone) is presented in a pre-dissolved state, ready for absorption; and (b) in any event, naloxone, and other opioid antagonists mentioned herein are known to be highly bioavailable drugs, with a rapid onset of action, when administered via the nasal mucosa. Accordingly, the compositions represent a therapeutic improvement on something that is already highly bioavailable and rapidly acting.

As is further described hereinafter, compositions of the invention that include alkyl saccharides have also been found to exhibit surprisingly good bioavailability and speed of absorption compared to corresponding compositions that do not include alkyl saccharides, and/or include different excipients that are known to act as surfactants. This is very surprising given that, when tested ex vivo, such alkyl saccharides showed a tendency to decrease permeation of opioid antagonist, such as naloxone, through mucosal membranes, whereas different surfactants, including some of those listed hereinafter, showed a tendency to increase permeation.

Alkyl saccharides that may be employed in the compositions of the invention include alkyl glycosides, which may be defined as any sugar joined by a linkage to an alkyl group, such as a $C_{7-18}$ alkyl glycoside. Alkyl glycosides thus may include alkyl maltosides (such as dodecyl maltoside), alkyl glucosides, alkyl sucrosides, alkyl thiomaltosides, alkyl thioglucosides, alkyl thiosucroses and alkyl maltotriosides. However, we prefer that the alkyl saccharide is a sugar ester.

Sugar esters that may be used in the compositions of the invention include trisaccharide esters, such as raffinose esters, monosaccharide esters, such as glucose esters, galactose esters and fructose esters, and/or, preferably, disaccharide esters, such as maltose esters, lactose esters, trehalose esters and, in particular, one or more sucrose esters.

Sucrose esters that are employed in compositions of the invention have a hydrophilic-lipophilic balance value of between 6 and 20. The term 'hydrophilic-lipophilic balance' (HLB) is a term of art that will be well understood by those skilled in the art (see, for example, "*The HLB System: A Time-Saving Guide to Emulsifier Selection*", published by ICI Americas Inc, 1976 (revised 1980), in which document, Chapter 7 (pages 20-21) provides a method of how to determine HLB values). The longer the fatty acid chains in the sucrose esters and the higher the degree of esterification, the lower the HLB value. Preferred HLB values are between 10 and 20, more preferably between 12 and 20.

Sucrose esters thus include $C_{8-22}$ saturated or unsaturated fatty acid esters, preferably saturated fatty acid esters and preferably $C_{10-18}$ fatty acid esters and most preferably $C_{12}$ fatty acid esters. Particularly suitable fatty acids from which such sucrose esters may be formed include erucic acid, behenic acid, oleic acid, stearic acid, palmitic acid, myristic acid and lauric acid. A particularly preferred such fatty acid is lauric acid. Commercially-available sucrose esters include those sold under the trademark Surfhope® and Ryoto® (Mitsubishi-Kagaku Foods Corporation, Japan).

Sucrose esters may be diesters or monoesters of fatty acids, preferably monoesters, such as sucrose monolaurate. The skilled person will appreciate that the term 'monolaurate' refers to a mono-ester of lauric acid, and that the terms 'lauric acid ester' and 'laurate' have the same meaning and can therefore be used interchangeably. Commercially available sucrose monolaurate products are also sometimes referred to as 'sucrose laurate'. Commercially-available sucrose monolaurate (or sucrose laurate) products, such as Surfhope® D-1216 (Mitsubishi-Kagaku Foods Corporation, Japan), which may contain small amounts of diesters and/or higher sucrose esters, and minor amounts of other sucrose esters and free sucrose, are suitable for use in the invention. The skilled person will understand that any reference to a specific sucrose ester herein includes commercially available products comprising that sucrose ester as a principle component.

Preferred sucrose esters contain only one sucrose ester, which means that a single sucrose ester (e.g. a commercially-available sucrose ester product) contains a single sucrose ester as the/a principle component (commercially available products may contain impurities, for example a monoester product may contain small amounts of diesters and/or higher esters, such products may be considered to 'contain only one sucrose ester' in the context of the present invention). As used herein, the term 'principle component' will be understood to refer to the major component (e.g. greater than about 50%, such as about 70% weight/weight or volume/volume) in a mixture of sucrose esters, such as common commercially available surfactant products, which are typically sold with a certain range of ester compositions.

A particularly preferred sucrose ester is sucrose monolaurate.

Amounts of alkyl saccharide in compositions of the invention are in the range of about 0.1% up to about 50%, more particularly up to about 10%, such as about 0.5% to about 5%, preferably about 0.75% to about 3% (e.g. to about 2%, such as about 1%), by weight, based upon the total weight of the composition.

In addition to any alkyl saccharide component that is included within a composition of the invention, further, optional, additional excipients may be employed.

Such additional excipients may include one or more (further) surfactants. Surfactants that may be mentioned include polyoxyethylene esters (e.g. Myrj™), including polyoxyl 8 stearate (Myrj™ S8), polyoxyl 32 stearate (Gelucire® 48/16), polyoxyl 40 stearate (Myrj™ S40), polyoxyl 100 stearate (Myrj™ S100), and polyoxyl 15 hydroxystearate (Kolliphor® HS 15), polyoxyethylene alkyl ethers (e.g. Brij™), including polyoxyl cetostearyl ether (e.g. Brij™ CS12, CS20 and CS25), polyoxyl lauryl ether (e.g. Brij™ L9 and L23), and polyoxyl stearyl ether (e.g. Brij™ S10 and S20), and polyoxylglycerides (e.g. Gelucire®), including lauroyl polyoxylglycerides (Gelucire® 44/14) and stearoyl polyoxylglycerides (Gelucire® 50/13), sorbitan esters (e.g. Span™), including sorbitan monopalmitate (Span™ 40) and sorbitan monostearate (Span™ 60), polysorbates (Tweens™), including polysorbate 40 (polyoxyethylene (20) sorbitan monopalmitate), polysorbate 60 (polyoxyethylene (20) sorbitan monostearate) and polysorbate 20 (polyoxyethylene (20) sorbitan monolaurate), and sodium lauryl sulfate; and monoacyl glycerols (monoglycerides), such as 2-oleoylglycerol, 2-arachidonoylglycerol, monolaurin, glycerol monomyristate, glycerol monopalmitate, glyceryl hydroxystearate and, preferably, glycerol monostearate, glycerol monooleate (e.g. Cithrol®) and glycerol monocaprylate (e.g. Capmul®).

Other additional ingredients (excipients) that may be included in compositions of the invention include isotonicity and/or osmotic agents (e.g. sodium chloride), sterols (or steroid alcohols), such as cholesterol and phytosterols (e.g. campesterol, sitosterol, and stigmasterol); antioxidants (e.g. α-tocopherol, ascorbic acid, potassium ascorbate, sodium ascorbate, ascorbyl palmitate, butylated hydroxytoluene, butylated hydroxyanisole, dodecyl gallate, octyl gallate, propyl gallate, ethyl oleate, monothioglycerol, vitamin E polyethylene glycol succinate, or thymol); chelating (complexing) agents (e.g. edetic acid (EDTA), citric acid, tartaric acid, malic acid, maltol and galactose); preservatives (e.g. benzyl alcohol, boric acid, parabens, propionic acid, phenol, cresol, or xylitol); viscosity modifying agents or gelling agents (such as cellulose derivatives, including hydroxypropylcellulose, methylcellulose, hydroxypropyl methylcellulose, carboxymethylcellulose, etc., starches and modified starches, colloidal silicon dioxide, aluminium metasilicate, polycarbophils (e.g. Noveon®), carbomers (e.g. Carbopol®) and polyvinylpyrrolidone); mucoadhesive polymers, such as carboxymethyl cellulose, modified cellulose gum and sodium carboxymethyl cellulose (NaCMC); starch derivatives, such as moderately cross-linked starch, modified starch and sodium starch glycolate; crosslinked polyvinyl pyrollidone, acrylic polymers, such as carbomer and its derivatives (Polycarbophyl, Carbopol®, etc.); polyethylene oxide (PEO); chitosan (poly-(D-glucosamine)); natural polymers such as gelatin, sodium alginate, pectin; scleroglucan; xanthan gum; guar gum; poly co-(methylvinyl ether/maleic anhydride); and croscarmellose (e.g. croscarmellose sodium); pH buffering agents (e.g. citric acid, maleic acid, malic acid, or glycine); colouring agents; penetration enhancers (e.g. isopropyl myristate, isopropyl palmitate, pyrrolidone, or tricaprylin); other lipids (neutral and polar); and aromatic carboxylic acid, such as benzoic acid optionally substituted with one or more groups selected from methyl, hydroxyl, amino, and/or nitro, for instance, toluic acid or salicylic acid.

Total amounts of such 'additional' excipients (including surfactants that are not the one or more alkyl saccharide(s) that is/are (or may be) present in compositions of the invention) may be up to about 15% (e.g. about 10%), such as up to about 5%, by weight, based on the total weight of the composition.

The skilled person will appreciate that, if any additional optional ingredients are included within compositions of the invention, the nature of those ingredients, and/or the amounts of those ingredients that are included, should not have a detrimental effect on the Tg of the composition for the reasons described hereinbefore. In this respect, when compositions of the invention are made by spray-drying, such optional ingredients may be incorporated in the spray-drying process (i.e. mixed together along with the opioid antagonist, the optional alkyl saccharide and the pharmaceutically-acceptable carrier material in the appropriate volatile solvent and then spray-dried), or may be included separately to the spray-dried plurality of particles.

According to a further aspect of the invention, there is provided the compositions of the invention for use in medicine (human and veterinary), and in particular in the treatment of substance (such as opioid, including opiate) overdose.

Overdose will be understood in the art to include what occurs when larger quantities of abusable substance, such as opioid, than may be physically tolerated by an individual are taken, resulting in (in the case of opioids) central nervous system and respiratory depression, hypoxia, miosis, and apnoea, one or more of which lead to death if not treated rapidly (vide supra).

According to a further aspect of the invention there is provided a method of treatment of substance (e.g. opioid) overdose, which method of treatment comprises administration of a composition of the invention to a patient suffering from such a condition.

By 'treatment' of substance (e.g. opioid) overdose, we include the prophylaxis or the diagnosis of such overdose (i.e. if an overdose is suspected), in addition to therapeutic, symptomatic and palliative treatment. This is because, by employing compositions of the invention in the treatment of drug overdose, they may abrogate or prevent the development of the symptoms of opioid overdose mentioned hereinbefore.

Care should be taken when administering compositions of the invention comprising partial opioid antagonists, such as buprenorphine, with a view to ensuring that the patient has definitely overdosed on an opioid (and not, for example, on a benzodiazepine), and/or that the patient is physically addicted to opioids.

Opioid antagonists may also be administered for use in the treatment of conditions mediated by endogenous opioid agonists (e.g. endorphins), which conditions may be collectively classified together as 'endorphin-mediated hedonia', as manifest by addictive behaviours (e.g. excessive eating (bulimia), drinking (alcoholism), exercise, sex, gambling, etc.).

Thus, according to a further aspect of the invention there is provided a method of treatment of addiction and/or an addictive behaviour mediated by activation of endogenous opioid agonists, such as endorphins (including bulimia, alcohol dependence, and addictions to exercise, sex, gambling, etc.), which method of treatment comprises administration of a composition of the invention to patient suffering from, or susceptible to, the relevant condition.

In the case of such addictions and addictive behaviours, by 'treatment', we include in particular the prophylaxis (prevention) and diagnosis of such conditions, in addition to the palliative and, particularly, the symptomatic treatment of such conditions.

Compositions of the invention may be administered intranasally by way of any suitable intranasal dosing means that is known to the skilled person, such as by way of a nasal applicator, or dispenser, means that is capable of administering a suitable dose of opioid antagonist in the form of a composition of the invention to the nasal cavity.

Such an applicator means should thus be capable of housing, and storing, the composition of the invention itself, or capable of being attached to a reservoir/container that houses and stores the composition of the invention, for example in the form of a powder, and do so without the consequence of a significant loss of physical and chemical integrity of the composition, including by way of ingress of water. In this way, the composition will be usable as soon as the applicator device is actuated by an end user, whereupon the applicator will deliver composition (e.g. powder) with an appropriate dose of opioid antagonist as defined herein to the nasal mucosa of a subject.

Appropriate applicator means have been described in the prior art. When used with compositions of the invention (particularly those in the form of a powder), such compositions may be loaded into a reservoir that is attached to, or forms part of, such an applicator means, where it is contained until the applicator means, or dispenser, is actuated. Hereinafter the terms 'applicator', 'dispenser', 'device' 'applicator means', 'dispensing means', 'applicator device' and 'dispensing device' may be used interchangeably and mean the same thing.

Such applicator means may thus also include a mechanism for expelling the powder formulation from the reservoir through an exit means, which exit means includes anything sized for placement within a human nostril, such as an appropriately-shaped nozzle.

Thus, the applicator should be capable of providing a reproducible and sufficient amount of powder formulation in a single administration step (and in a manner in which the device does not require 'priming'), that will provide a therapeutic dose of opioid antagonist.

Nasal applicators/inhalation devices that may be employed to administer compositions of the invention in the form of powders may include multiple-dose applications, such as metered dose inhalation devices (MDIs), dry powder inhalation devices (DPIs; including low, medium and high resistant DPIs) and soft mist inhalation devices (SMIs) that may be adapted based on technology that is known in the field of delivery of active ingredients to the lung.

In MDIs, compositions of the invention should be capable of forming a stable suspension when suspended in solvents that are typically employed therein, such as a propellant, which propellant has a sufficient vapour pressure to form aerosols upon activation of the delivery device (e.g. a hydrocarbon, a fluorocarbon, a hydrogen-containing fluorocarbon, or a mixture thereof).

However, we prefer that the nasal applicator is a single dose applicator from which a composition is dispensed following actuation, and is then disposed of after use.

In this respect, suitable applicator means or devices include those described in U.S. Pat. No. 6,398,074, 6,938, 798 or 9,724,713, the relevant disclosures in all of which documents are incorporated herein by reference. FIGS. 1 and 2 of the present application are based on FIG. 1 and FIG. 2, respectively, of U.S. Pat. No. 6,398,074, and FIGS. 3 to 7 are based on FIG. 19 to FIG. 23, respectively, of U.S. Pat. No. 9,724,713. Both are illustrations of applicators that be may be employed to administer a composition of the invention intranasally.

In FIG. 1, the device comprises an upper body/dispenser head 1 incorporating an outlet channel 40 (i.e. part of the 'exit means' as hereinbefore described) and a gripping means 60 allowing the user to actuate the device. Inside the upper body/dispenser head 1 an element is mounted, designated in its assembly by reference number 2, that incorporates a reservoir 10 and an air chamber 22 for the air blast 20. It is possible for this element 2 to be produced in one piece with the body 1. A lower body 3 is also provided in order to be able to slide relative to the upper body 1 and relative to the element 2, the user exerting a push force on the lower body to actuate the device.

The reservoir 10 contains a single dose of a composition of the present invention. The reservoir 10 has an air inlet 11 and a product outlet 15. A product retention device 12, comprising a grid that is permeable to air, is disposed in the air inlet 11 to keep the product in the reservoir 10 until the composition is dispensed. The product outlet 15 is blocked, preferably in a sealed fashion, by a closing ball 16, which is removed from its blocking position by the flow of air when the applicator is actuated and the product is being dispensed.

When a user actuates the device, a pressure is exerted on the plunger 25 in such a way that the piston 21 compresses the air 20 contained in the chamber 22. Since the grid 12 is permeable to air, the compression of the air in chamber 22 creates a blast of air that is transmitted to the reservoir 10 and consequently is applied to the closing ball 16 which is blocking the product outlet 15.

The dimensions of the closing ball 16 and its fixing at the reservoir product outlet 15 are such that the ball 16 is removed from its blocking position, when a minimum predetermined pressure is created through the reservoir 10 by way of a blast of the air 20.

The pre-compression created by the closing ball 16 ensures that when it is removed from its blocking position, the energy accumulated in the hand of the user is such that the piston 21 integral with the plunger 25 is propelled within the chamber 22 thereby creating a powerful blast of air 20, that is to say an air flow suitable to finely spray the dose of composition of the invention.

When this minimum pressure is reached, the ball is quickly moved towards the outlet channel 40 of the device and the flow of air 20 created by the blast expels substantially all of the dose of composition of the invention that is contained within the reservoir 10.

Preferably, the outlet channel 40 has a diameter greater than the diameter of the closing ball 16 in order to allow the dose of product to be expelled through the outlet channel 40 by flowing around the ball 16. As shown in FIG. 2, which represents the same device after actuation, the channel 40 comprises a means 41 of arresting or fixing the ball 16 in order to prevent its expulsion out of the device when the product is being expelled.

A further embodiment that may be employed to administer compositions of the invention intranasally is provided in U.S. Pat. No. 9,724,713 at column 7, line 50 to column 8, line 61 and FIGS. 19 to 23, which are reproduced as FIGS. 3 to 7 of the present application.

In this embodiment, the reservoir 10 is secured in the upper body/dispenser head 1 which includes the dispenser outlet channel 40 (i.e. part of the 'exit means' as hereinbefore described), which has gripping means or finger rest 60, which allows the user to actuate the device. A radial shoulder 37 (see FIG. 5) of the upper body/dispenser head 1 advantageously defines the assembled position of the reservoir 10 in said of the upper body/dispenser head 1.

The mechanical opening system includes a set of rods 61, 62, wherein a second rod portion 62 is pushed by said first rod portion 61 when the device is actuated. At the end of their actuation stroke, i.e. in the dispensing position, the set of rods 61, 62 co-operate with the closure element 16, which is spherical, in particular a ball as in the first embodiment discussed above, so as to expel it mechanically from its closed position.

Figure 7:
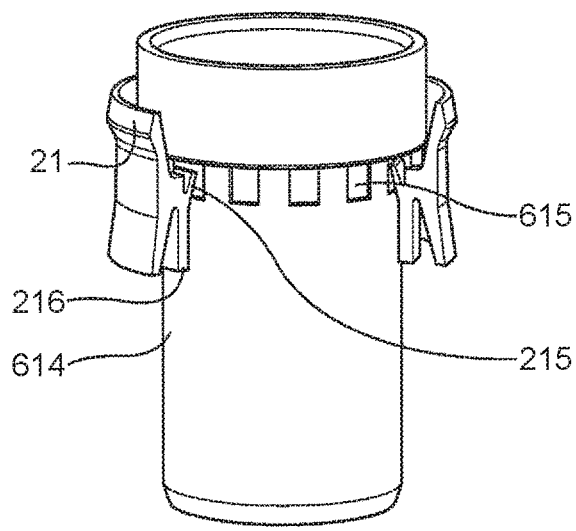
FIG. 7 is a diagrammatic perspective view of the air expeller of the device in FIGS. 3 to 6 shown in its rest position.

In this embodiment, the piston 21 is separate from the first rod portion 61, and slides both relative to the air chamber 22 and to a cylindrical surface 614 that is secured to the first rod portion 61. FIG. 7 is a diagrammatic perspective view of the air expeller of the device in FIGS. 3 to 6, in its rest position.

The air chamber 22 may thus be cylindrical, and in its rest position is put into communication with the surrounding air at fluting or grooves 615 that are formed in said cylindrical surface 614 and that co-operate with the piston 21, in particular in its rest position. The piston 21 thus includes an inner lip 215 that slides in airtight manner over the cylindrical wall 614 during actuation, and that co-operates with said fluting 615 in its rest position. The piston 21 also includes an axial extension 216 that co-operates with a top edge 251 of the pusher element 25 (termed a 'plunger' in the first embodiment) that moves said piston 21 in the air chamber 22 during actuation.

A retainer member 42 is extended downwards by an axial extension 43 that comes into contact with the top axial end 610 of the first rod portion 61 during actuation.

In addition, in this embodiment, there is no outer body, but merely a cover 27 that is assembled on the bottom axial edge of the air chamber 22.

A spring 80 is provided between the radial flange 225 of the air chamber 22 and the part that forms the first rod portion 61 and the cylindrical surface 614, so as to return the air expeller automatically into its rest position after actuation.

The operating principle is as follows. In the rest position in FIG. 3, the reservoir 10 is closed in sealed manner by the retainer member 42 and by the closure element/ball 16. The air expeller is open to the atmosphere by co-operation between the inner lip 215 of the piston 21 and the fluting 615 of the cylindrical surface 614.

When it is desired to actuate the device, the user presses on the pusher element 25. During this initial stroke, the inner lip 215 of the piston leaves the fluting 615 so as to come to co-operate in airtight manner with the cylindrical surface 614, thereby closing the air chamber 22. At the same moment, the top edge 251 of the pusher element 25 comes into contact with the axial extension 216 of the piston 21, and the top axial end 610 of the first rod portion 61 comes into contact with the axial extension 43 of the retainer member 42.

However, the top axial end 621 of the second rod portion 62 is still not in contact with the rounded surface 55 of the closure element/ball 16, as can be seen in FIG. 4.

Continued actuation thus simultaneously moves the piston 21 in the air chamber, thereby compressing the air contained therein, and moves the retainer member 42 away from its position of closing the reservoir 10. When the second rod portion 62 contacts the rounded surface 55 of the closure element/ball 16, said closure element/ball is expelled mechanically from its closed position, so as to enable the composition to be expelled under the effect of the air compressed by the air expeller.

The dispensing position is shown in FIG. 5. As can be seen in FIG. 5, the retainer member 42 may become detached from the first rod portion 61 while the composition is being expelled under the effect of the compressed air provided by the air expeller. In this position, said closure element/ball is expelled out from the reservoir 10 so as to enable the fluid or powder to be dispensed under the effect of the compressed air. The closure element/ball 16 thus becomes jammed in splines 3 of the upper body/dispenser head 1, which splines prevent in particular any risk of said closure element/ball 16 being expelled out from said upper body dispenser head 1.

When the user relaxes the device, as shown in FIG. 6, the spring 80 that was compressed during actuation, returns the first rod portion 61 towards its rest position. This creates suction that sucks the closure element 16 and the retainer member 42 back towards, or close to, their closure positions. This thus blocks the path for new suction so as to avoid soiling the air expeller while it returns automatically into its rest position, with the empty reservoir still assembled on the air expeller. However, the piston 21 remains in its dispensing position as a result of friction with the air chamber 22 and of the suction created in the reservoir 30, such that the cylindrical surface 614 slides over the inner lip 215 of the piston until said inner lip co-operates once again with the fluting 615. At this moment, the air chamber 22 is once again in communication with the surrounding air, and suction is no longer created by the return into the rest position. The piston 21 is thus also entrained towards its rest position. This makes it possible to close the reservoir after use.

Optionally, the unit formed by the upper body/dispenser head 1 and the empty reservoir 10 could be removed from the air expeller and replaced by a new unit that includes a full reservoir.

Appropriate applicator devices that may be used include those available from Aptar Pharma, France (UDS Monopowder). Other examples of applicator devices that may be used in conjunction with compositions of the invention (especially those in the form of powders) include those described in US patent application US 2011/0045088A, U.S. Pat. No. 7,722,566 (see e.g. FIGS. 1 and 7) and U.S. Pat. No. 5,702,362 and international patent application WO 2014/004400, the relevant disclosures of which documents are hereby incorporated by reference.

According to a further aspect of the invention, there is provided a process for the manufacturing of an applicator device comprising a composition of the invention, wherein said process comprises the step of loading said composition into a reservoir within or adjunct to said applicator device.

According to another aspect of the invention, there is provided an applicator and/or dispenser device comprising a composition of the invention in the form of a powder, suitable for dispensing that powder, which applicator/dispenser device comprises:

an outlet through which composition of the invention is dispensed;

a means of externally generating a force (e.g. an air-flow) upon actuation of the device by a user;

at least one (optionally replaceable) reservoir that contains a composition of the invention, which reservoir is, or is capable of being placed, in direct or indirect communication with the dispenser outlet;

a displaceable sealing means in the device and/or the reservoir for retaining the composition within the reservoir until the composition is dispensed; and a mechanical opening system that co-operates with said sealing means such that the composition of the invention is expelled mechanically by the forcing means when the device is actuated.

According to a still further aspect of the invention there is provided an applicator and/or dispenser device comprising a composition of the invention in the form of a powder, suitable for dispensing that powder, which applicator/dispenser device comprises:

a dispenser outlet;

an air expeller for generating a flow of air while the device is being actuated, said air expeller including a piston that slides in an air chamber between a rest position and a dispensing position;

said piston slides in airtight manner within said air chamber;

at least one reservoir that contains a dose of a composition of the invention, said reservoir including an air inlet that is connected to said air expeller;

a composition outlet that is connected to said dispenser outlet;

said air inlet including a displaceable sealing means (e.g. a retainer member) for retaining the composition in the reservoir until the composition is dispensed;

said composition outlet being closed by a closure element that is fitted in the composition outlet of the reservoir;

said device further including a mechanical opening system that co-operates with said closure element so as to expel it mechanically from its closed position while the device is being actuated; and said piston of said air expeller, when in its rest position, co-operating in non-airtight manner with said air chamber.

In the latter aspect of the invention, it is preferred that:

(i) the air chamber within which said piston slides in airtight manner is substantially cylindrical;

(ii) the closure element is force fitted in the composition outlet of the reservoir;

(iii) said air chamber is in communication with the atmosphere in the rest position; and/or (iv) said piston includes an inner lip that is suitable for co-operating with a cylindrical surface, said cylindrical surface includes fluting that co-operates in non-airtight manner with said inner lip of the piston in its rest position.

Such an applicator or dispensing device is capable of providing for an appropriate and reproducible powder spray pattern and/or plume geometry that enables efficient delivery of said powder to the nasal cavity (e.g. a nostril).

In compositions of the invention, mean particle sizes may be presented as weight-, number-, or volume-, based mean diameters. As used herein, the term 'weight based mean diameter' will be understood by the skilled person to include that the average particle size is characterised and defined from a particle size distribution by weight, i.e. a distribution where the existing fraction (relative amount) in each size class is defined as the weight fraction, as obtained by e.g.

sieving (e.g. wet sieving). The term 'volume based mean diameter' is similar in its meaning to weight based mean diameter, but will be understood by the skilled person to include that the average particle size is characterised and defined from a particle size distribution by volume, i.e. a distribution where the existing fraction (relative amount) in each size class is defined as the volume fraction, as measured by e.g. laser diffraction. As used herein, the term 'number based mean diameter' will be understood by the skilled person to include that the average particle size is characterised and defined from a particle size distribution by number, i.e. a distribution where the existing fraction (relative amount) in each size class is defined as the number fraction, as measured by e.g. microscopy. Other instruments that are well known in the field may be employed to measure particle size, such as equipment sold by e.g. Malvern Instruments, Ltd (Worcestershire, UK), Sympatec GmbH (Clausthal-Zellerfeld, Germany) and Shimadzu (Kyoto, Japan).

In the context of the present invention, the skilled person will understand that, to allow for intranasal administration, powders will typically have a volume-based mean diameter (VMD) within the range of about 5 μm (e.g. about 10 μm) up to about 1,000 μm (e.g. up to about 500 μm). Depending on the applicator device that is employed, the VMD may be in the range of about 10 μm to about 100 μm, such as about 20 μm to about 60 μm.

Preferred particle size distributions may also include those in which the d10 is above about 3 μm and below about 75 μm (e.g. up to about 50 μm), such as greater than about 10 μm, and the d90 is between about 80 μm and about 1,000 μm (e.g. about 500 μm), such as less than about 100 μm. The skilled person will understand that the parameter 'd10' (or 'Dv(10)') means the size (or diameter) in a particle size distribution below which 10% of the total volume of material in the sample is contained. Similarly, the 'd90' (or 'Dv(90)') means the size below which 90% of the material is contained.

By powders having particle size diameters and/or VMDs within the above ranges, we include the bulk VMD and/or the emitted VMD, that is the particle size distribution when initially loaded into the device and/or when it is expelled therefrom, respectively.

Particle sizes may be measured by standard equipment, such as a dry (or a wet) particle size measurement technique, including dry dispersion technologies available from manufacturers, such as Sympatec and Malvern.

Preferred particle shapes include spherical or substantially spherical, by which we mean that the particles possess an aspect ratio smaller than about 20, more preferably less than about 10, such as less than about 4, and especially less than about 2, and/or may possess a variation in radii (measured from the centre of gravity to the particle surface) in at least about 90% of the particles that is no more than about 50% of the average value, such as no more than about 30% of that value, for example no more than about 20% of that value.

Nevertheless, particles may be any shape, including irregular shaped (e.g. 'raisin'-shaped), needle-shaped, disc-shaped or cuboid-shaped, particles. For a non-spherical particle, the size may be indicated as the size of a corresponding spherical particle of e.g. the same weight, volume or surface area.

The spray angle of emitted (dispensed) powder composition of the invention from an applicator and/or a dispenser device should preferably be less than about 90°.

Compositions of the invention may be formulated with additional active ingredients, such as those known to treat opioid withdrawal symptoms, such as lofexidine, and/or partial opioid antagonists that are employed in the treatment of opioid dependence, for example, buprenorphine (vide supra).

Accordingly, co-administering at least one (preferably full) opioid antagonist as described hereinbefore alongside such an opioid withdrawal symptom treatment (such as lofexidine or buprenorphine) may serve to abrogate the strong withdrawal symptoms that may be observed when administering a composition of the invention in the absence of such a compound.

Compositions of the invention may thus be provided along with a compound that is suitable for use in the treatment of opioid withdrawal symptoms (such as lofexidine or buprenorphine, or a pharmaceutically acceptable (e.g. HCl) salt of either compound, wherein the latter compound/treatment is included within the composition (i.e. presented as a single pharmaceutical composition including both active ingredients). Alternatively, compositions of the invention may be co-administered along with a separate composition comprising a compound that is suitable for use in the treatment of opioid withdrawal symptoms (such as lofexidine or buprenorphine) or a salt thereof.

Thus, there is further provided a pharmaceutical preparation comprising a composition of the invention as hereinbefore defined, which composition further includes a compound that is suitable for use in the treatment of opioid withdrawal symptoms (such as lofexidine or buprenorphine) or a pharmaceutically acceptable salt thereof, such a preparation is hereinafter referred to as a 'combined preparation'.

There is further provided a process for the preparation of a combined preparation as hereinbefore defined, which process comprises bringing into association an opioid antagonist as hereinbefore defined and a compound that is suitable for use in the treatment of opioid withdrawal symptoms (e.g. lofexidine, buprenorphine or salt thereof) along with the other ingredients of a composition of the invention, and optionally loading into a container that is for use within, or along with (e.g. attached to), an applicator device as hereinbefore described.

In such an instance, the combined preparation may have the same or similar physical attributes as those described hereinbefore for compositions of the invention that do not include a compound suitable for treatment of opioid withdrawal symptoms, in respect of which the relevant disclosures herein are incorporated by reference.

In a further aspect of the invention, there is also provided a kit of parts comprising components (A) and (B) as follows:
(A) a composition of the invention; and
(B) a pharmaceutical composition including a compound that is suitable for use in the treatment of opioid withdrawal symptoms (e.g. lofexidine or buprenorphine) or a pharmaceutically acceptable salt thereof in admixture with a pharmaceutically-acceptable diluent or carrier, wherein compositions (A) and (B) are optionally loaded, or are presented for loading, into separate containers, which containers are for use within, or along with (e.g. attached to), the same, or separate, applicator devices that is/are suitable for administration of compositions to the nasal cavity, e.g. as hereinbefore described.

In such an instance, the pharmaceutical composition comprising opioid withdrawal symptom treatment described under (B) above may have the same or similar physical attributes as those described hereinbefore for a composition of the invention, including that under (A) above. For example, the pharmaceutical composition comprising opioid withdrawal symptom treatment may be presented in the form of a powder containing particles with a similar particle size to those mentioned hereinbefore for compositions of the invention.

According to a further aspect of the invention, there is provided a method of making a kit of parts as defined above, which method comprises bringing component (A), as defined above, into association with a component (B), as defined above, thus rendering the two components suitable for administration in conjunction with each other.

As alluded to above, by bringing the two components 'into association with' each other, we include that components (A) and (B) of the kit of parts may be:
(i) provided as separate formulations (i.e. independently of one another), which are subsequently brought together for use in conjunction with each other in combination therapy; or
(ii) packaged and presented together as separate components of a 'combination pack' for use in conjunction with each other in combination therapy.

Thus, there is further provided a kit of parts comprising:
(I) one of components (A) and (B) as defined herein; together with
(II) instructions to use that component in conjunction with the other of the two components.

The kits of parts described herein may comprise more than one formulation including an appropriate quantity/dose of opioid antagonist/salt, and/or more than one formulation including an appropriate quantity/dose of compound suitable for treatment of opioid withdrawal symptoms, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by 'administration in conjunction with', we include that respective formulations comprising opioid antagonist (or salt thereof) and compound suitable for treatment of opioid withdrawal symptoms (or salt thereof) are administered, sequentially, separately and/or simultaneously, to treat the relevant condition.

Thus, in respect of the combination product according to the invention, the term 'administration in conjunction with' includes that the two components of the combination product are administered (optionally repeatedly), either together, or sufficiently closely in time, to enable a beneficial effect for the patient, that is greater than if either formulation is administered (optionally repeatedly) alone, in the absence of the other component. Determination of whether a combination provides a greater beneficial effect during treatment of a relevant condition will depend upon the condition to be treated or prevented, but may be achieved routinely by the skilled person.

After the emergency situation of treating acute opioid overdose has been dealt with, further compositions comprising compound suitable for treatment of opioid withdrawal symptoms (e.g. lofexidine or, more preferably, buprenorphine or salt thereof) may be administered as necessary or desired. Such compositions may be similar in form to compositions of the invention (and in respect of which the relevant disclosures herein are incorporated by reference) or otherwise (e.g. sublingual formulations).

When the compound suitable for treatment of opioid withdrawal symptoms is buprenorphine, suitable doses may be in the range of between about 1 mg to about 32 mg, more preferably about 5 mg to about 20 mg, calculated as the free base.

When the compound suitable for treatment of opioid withdrawal symptoms is lofexidine, suitable doses (e.g. daily doses) may be in the range of between about 0.1 mg to about 3 mg, such as about 0.5 mg to about 2 mg, calculated as the free base.

Wherever the word 'about' is employed herein in the context of amounts, for example absolute amounts, such as doses, weights, volumes, sizes, diameters, etc., or relative amounts of individual constituents in a composition or a component of a composition (including concentrations and ratios), timeframes, and parameters, such as temperatures, pressure, relative humidities, etc., it will be appreciated that such variables are approximate and as such may vary by ±10%, for example ±5% and preferably ±2% (e.g. ±1%) from the actual numbers specified herein. This is the case even if such numbers are presented as percentages in the first place (for example 'about 10%' may mean±10% about the number 10, which is anything between 9% and 11%).

Compositions of the invention have the advantage that they are capable of being stored over a wider range of temperatures than prior art compositions, including those that are commercially-available (e.g., in the case of naloxone, Narcan). Thus, compositions of the invention may be subject to low temperatures (e.g. below freezing) without impacting the amount of opioid antagonist that is administered to a subject. Further, compositions of the invention may have the advantage that they are more physically and chemically stable at higher temperature than such prior art compositions.

Compositions of the invention further have the significant advantage that they provide for higher bioavailability of opioid antagonist compared to prior art compositions, including those that are commercially-available (e.g., in the case of naloxone, Narcan). The compositions of the invention provide for this higher bioavailability alongside a more rapid absorption, which will likely lead to a more rapid onset of action than such prior art and/or commercially-available compositions, and thus meets a significant and serious medical need.

The compositions, pharmaceutical formulations, uses and methods described herein may also have the advantage that, in the treatment of the conditions mentioned hereinbefore, they may be more convenient for the first responder, physician and/or patient than, be more efficacious than, be less toxic than, have a broader range of activity than, be more potent than, produce fewer side effects than, have a lower inter-patient variability, or that it/they may have other useful pharmacological properties over, similar formulations or methods (treatments) known in the prior art, whether for use in the treatment of opioid overdose (or of bulimia or alcohol dependence), or otherwise.

Figure 8:
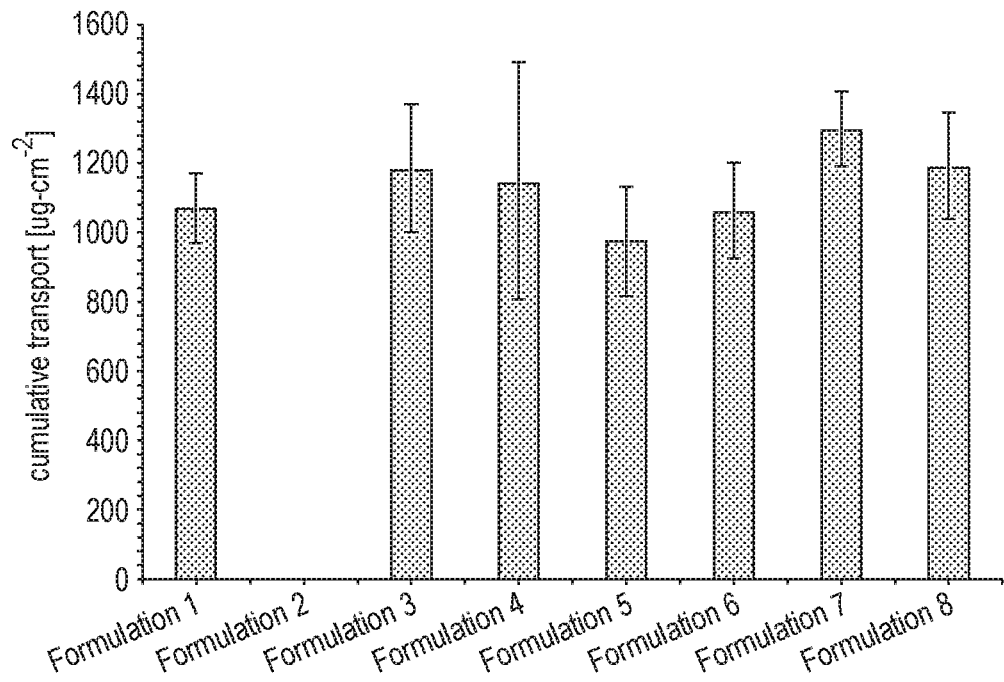
FIG. 8 is a graph showing permeation of naloxone through porcine nasal tissue in an ex vivo model.
Figure 9:
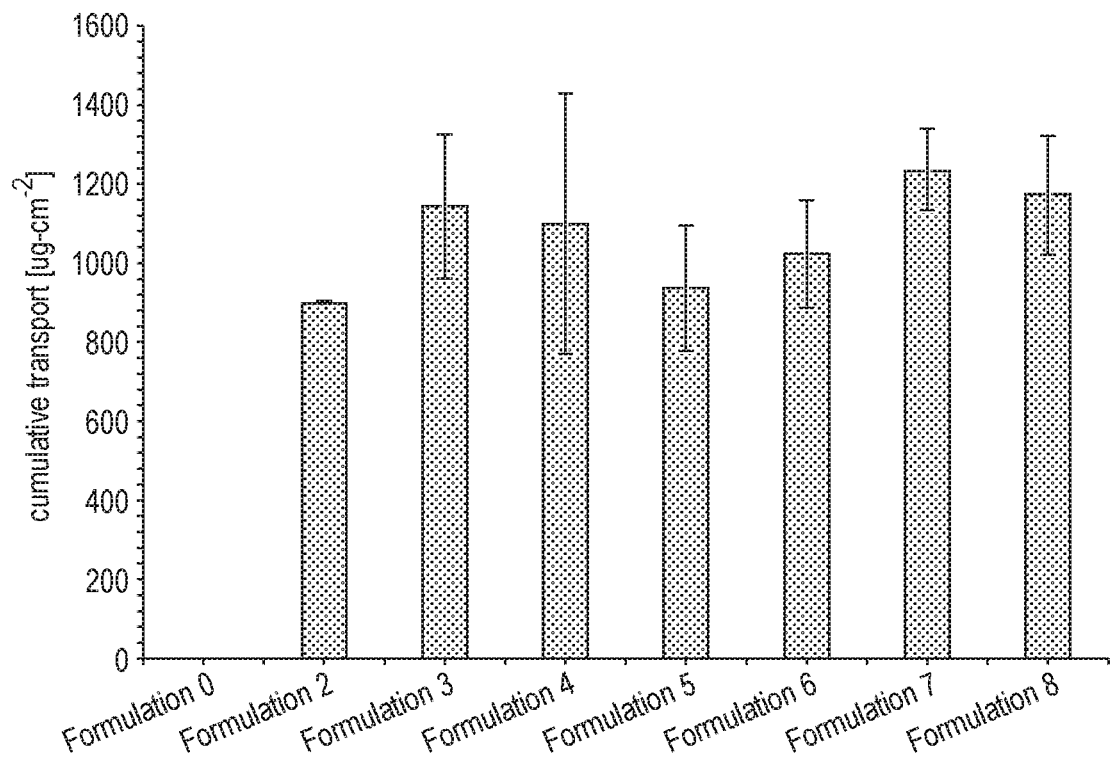
FIG. 9 is a graph showing permeation of nalmefene through porcine nasal tissue in an ex vivo model.
Figure 10:
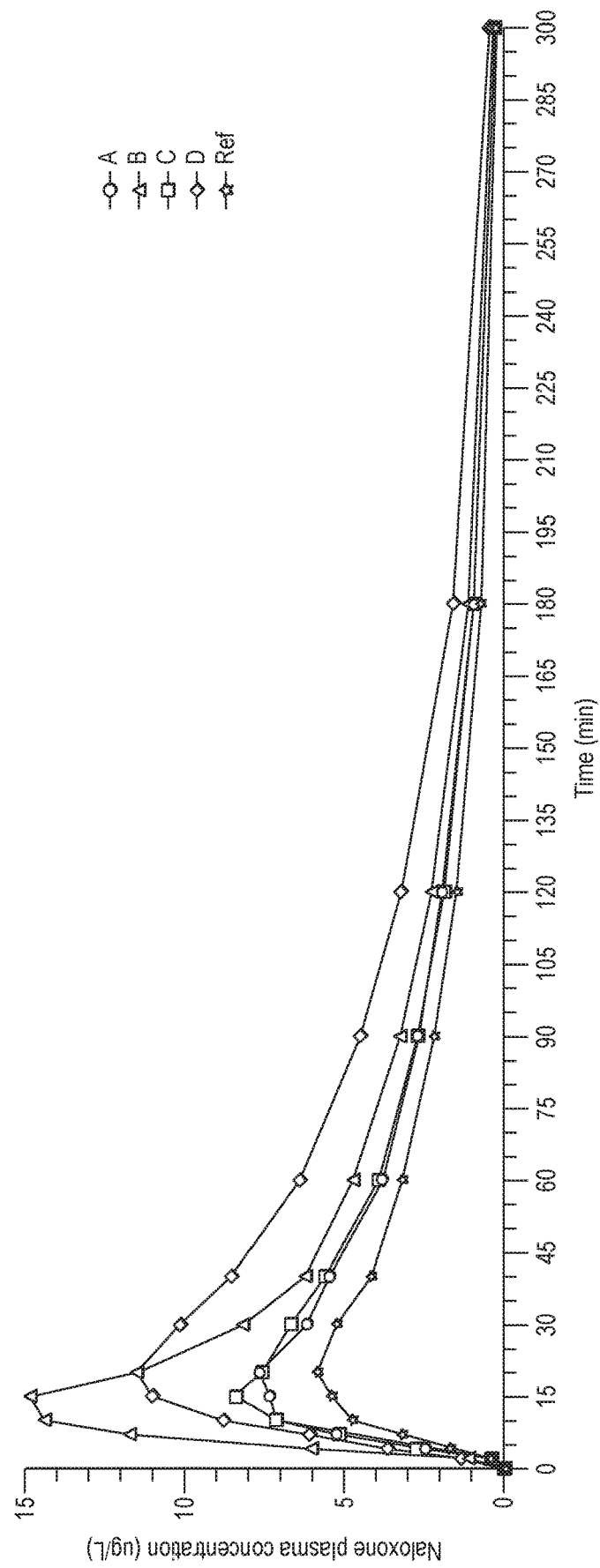
FIGS. 10 and 11 show mean naloxone plasma concentrations versus time, by treatment (linear scale), as obtained in a clinical trial, over different time periods.
Figure 11:
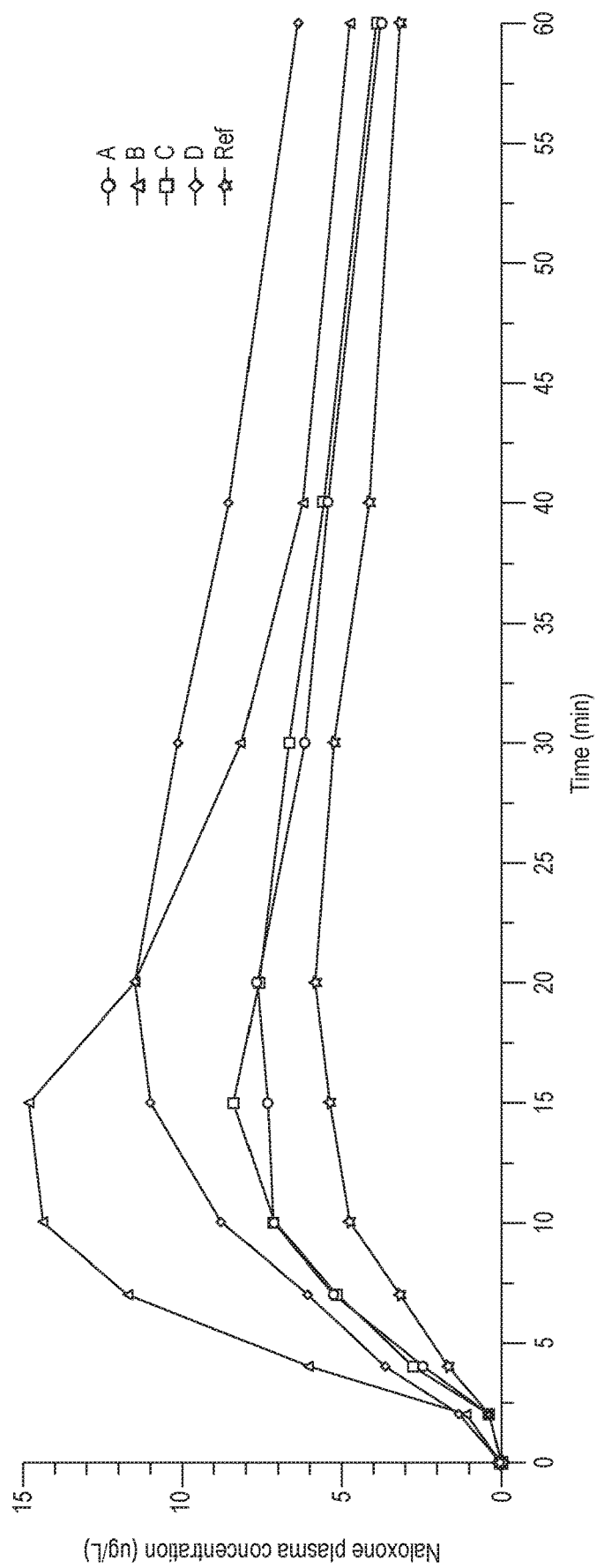

The invention is illustrated but in no way limited by way of the following examples, with reference to the attached figures, in which: FIGS. 1 to 7 represent drawings of actuator devices that may be used to dispense compositions of the invention, FIGS. 8 and 9 show permeation of naloxone, and nalmefene, respectively, through porcine nasal tissue in an ex vivo model; and FIGS. 10 and 11 show mean naloxone plasma concentrations versus time, by treatment (linear scale), as obtained in a clinical trial, over different time periods.

Example 1

Spray-Drying Opioid Antagonists with Various Saccharides
Naloxone HCl dihydrate (1.199 g; Johnson Matthey, UK) or nalmefene HCl (0.600 g; Santa Cruz Biotechnology Inc., USA) and naltrexone HCl (0.600 g; Mallinckrodt Inc., USA) were separately mixed, along with different saccharides (5.088 g for naloxone and 2.554 g for nalmefene and naltrexone), which were employed as carrier materials in the composition and purified water for irrigation (56.58 g for naloxone and 28.29 g for nalmefene and naltrexone), and the mixtures fed into a spray-dryer according to a general procedure as follows.

Solid ingredients were weighed into a beaker equipped with a magnetic stirring bar, dissolved in water and fed into a spray-dryer (ProCepT, Belgium) equipped with an ultrasonic nozzle operating at 25 kHz. The feed rate of the spray-dryer was set at 3.0 g/minute, the inlet temperature was set at 180° C., the gas flow was set at 300 L/min, and the cyclone gas was set at 1.5 bar.

The resultant spray-dried powder was collected and packed into devices suitable for nasal powder administration (single shot nasal unidose device for disposable use; UDS Monopowder, Aptar Pharma, France), with a fill weight of 23 mg. (For naloxone, this constituted a single dose of 4 mg of naloxone (calculated as the HCl salt).)

The devices were placed in heat-sealed aluminum pouches before storage for 6 months at 40° C. and 75% relative humidity (RH).

The chemical composition of the spray-dried mixtures after storage, and the amount of powder emitted from the devices after actuation, were determined.

The stability of naloxone after 6 months (6M), with amounts of impurities expressed as a percentage of the related substance (% RS) is summarized for the different saccharides in Table 1 below. Initial values of % RS were less than 0.1% for all samples.

TABLE 1

| Saccharide | Maltitol (Roquette, France) | Galactose (Acros Organics, Belgium) | Trehalose (Acros Organics, Belgium) | Sucralose (Merck, Germany) | Sucrose (Merck, Germany) |
|---|---|---|---|---|---|
| Stability 6M (% RS) | 2.44 | 0.20 | 0.09 | 5.40 | 1.04 |
| Emitted dose | 2.2 mg | 5.3 mg | 22.4 mg | 4.5 mg | 3.8 mg |

| Saccharide | Isomalt (BENEO-Palatinit, Germany) | Mannitol (Roquette, France) | Maltose (Merck, Germany) | Lactose (Acros Organics, Belgium |
|---|---|---|---|---|
| Stability (% RS) | 1.27 | 0.99 | 4.18 | 0.07 |
| Emitted dose | 6.1 mg | 21.2 mg | 3.9 mg | 21.4 mg |

Unexpectedly, certain monosaccharides, like mannitol, which has been previously used in physical mixtures together with naloxone, proved incompatible when employed in this spray-drying process (in terms of the chemical stability of naloxone). This was to be contrasted with disaccharides, like lactose, which were generally compatible.

Further, polysaccharides known to have a higher Tg tended to give rise to a higher emitted powder dose. Physical changes as a result of a low Tg gave caking and aggregation of the powder in the devices.

For nalmefene and naltrexone, a similar trend was observed (see Table 2 below, where initial % RS values are presented in parentheses).

TABLE 2

| API Saccharide | Nalmefene Lactose | Nalmefene Mannitol | Naltrexone Lactose | Naltrexone Mannitol |
|---|---|---|---|---|
| Stability (% RS) 6M 40/75 | 0.83 (0.77) | 1.82 (0.75) | 0.33 (0.11) | 1.12 (0.08) |
| Emitted dose | 21.7 mg | 21.6 mg | 20.4 mg | 19.3 mg |

Example 2

Physical Stability of Spray-Dried Powders

In order to assess the physical stability and mitigate the risk for crystallization during storage, glass transition temperatures (Tg) were determined using differential scanning calorimetry (DSC) and are presented in Table 3 below.

Compositions were prepared generally in accordance with the procedure described in Example 1 above, using mannitol, trehalose and lactose as carrier materials.

For lactose, the true Tg, as well as that of the formulation subjected to equilibration at four different RH conditions at 25° C. (10%, 20%, 30% and 40% RH), were measured (although 30% was not logged). For mannitol and trehalose, Tg was measured as received ('Ambient') and after drying ('Dried').

For the dried samples, the DSC ampoule lid was punched automatically immediately before start of the DSC run, introducing a hole of about 0.3 mm diameter. The purpose of this was to allow any remaining moisture to evaporate before the glass transition temperature for a dry formulation was reached. Hence, this Tg value corresponds to the true Tg without interference from available plasticizers like water.

For the samples equilibrated at different RH values, the DSC lid was gas-tight throughout the DSC run. Samples were prepared as described above.

TABLE 3

| Composition | RH (%) | Tg (° C.) |
|---|---|---|
| Mannitol | Dried | — |
|  | Ambient | — |
| Trehalose | Dried | 119 |
|  | Ambient | 51 |
| Lactose | Dried | 115 |
|  | 10 | 60 |
|  | 20 | 57 |
|  | 30 | 52 |
|  | 40 | 36 |

Using trehalose or lactose as carrier materials gave completely amorphous compositions, in contrast to mannitol which seemed to crystalize in the spray-dryer as no Tg could be found and the water content was below 1%.

Example 3

Ex-Vivo Evaluation of Nasal Mucosal Absorption of Naloxone and Nalmefene

A standard static diffusion (Franz) cell set up was employed to set up an ex vivo model for nasal mucosa absorption, using an excised porcine nasal tissue.

Solutions containing naloxone HCl dihydrate, nalmefene HCl, benzalkonium chloride (Sigma-Aldrich Sweden AB), sucrose monolaurate (IMCD Nordic AB) and/or polysorbate 80 (Croda Nordica AB) were prepared by standard techniques, to provide formulations according to Table 4 below. Potassium phosphate buffer (Sigma-Aldrich Sweden AB) was added to give the pH stated in Table 4 below.

TABLE 4

| Formulation | 1 | 2 | 3 | 4 | 5 | 6 | 7 | 8 |
|---|---|---|---|---|---|---|---|---|
| naloxone (mg/mL) | 5 | | 5 | 5 | 5 | 5 | 5 | 5 |
| nalmefene (mg/mL) | | 5 | 5 | 5 | 5 | 5 | 5 | 5 |
| benzalkonium chloride (mg/mL) | 0.1 | 0.1 | 0.1 | | | | | |
| sucrose monolaurate (mg/mL) | | | | | 0.4 | 2 | | |
| polysorbate 80 (mg/mL) | | | | | | | 2 | |
| pH | 4.5 | 4.5 | 4.5 | 4.5 | 4.5 | 4.5 | 4.5 | 6.5 |

Diffusion through the tissue was measured after 7 hours and permeation is shown as mean (three repeats) cumulative transport (μg/cm$^2$; with SD) in FIGS. 8 and 9 for naloxone and nalmefene, respectively.

For both naloxone and nalmefene, slightly higher apparent permeation coefficients (Papp) were observed in Formulations 7 and 8, which contained polysorbate 80 and a higher amount of pH buffer, respectively. No corresponding absorption enhancement was observed in the case of benzalkonium chloride or sucrose monolaurate.

Example 4

Naloxone-Containing Composition B

The general procedure described in Example 1 was employed to make a spray-dried composition from naloxone HCl dihydrate (1.199 g), along with α-D-lactose monohydrate (5.026 g; DFE Pharma Germany), sucrose monolaurate D-1216 (0.062 g; Mitsubishi-Kagaku Foods Corporation, Japan).

Composition B comprised a single dose of naloxone of 4 mg (calculated as the HCl salt).

Devices were placed in heat-sealed aluminum pouches (Protective Packaging, UK) before use.

The geometric particle size distribution (PSD) was measured using a Malvern Mastersizer 2000 (Malvern Panalytical Ltd, UK) and aerodynamic particle size distribution (aPSD) using a fast screening impactor (FSI, Copley Scientific, UK). PSD: d10=15 μm and d90=55 μm; aPSD <5 μm=0%.

General method for PSD measurements: 80 to 100 mg of sample was dispersed in 5 mL of silicone oil and mixed well before sonication for 20 to 30 seconds. Three measurements were made on the solution using a Malvern Mastersizer 2000 (Malvern Panalytical Ltd., UK).

General method for aPSD measurements: A loaded device was actuated in a fast screening impactor (FSI, Copley Scientific, UK) fitted with a suitable adaptor, an expansion bulb and a 10 micron insert. Flow was adjusted to 30±0.5 L/min. Results were reported as fine particle mass (FPM) as % recovered in the filter stage (<5 μm).

Example 5

Naloxone-Containing Compositions a, C and D

The same general procedure as that described in Example 4 above was followed to prepare three further spray-dried powders, with compositions according to Table 5 below.

TABLE 5

| Component | Quantity per batch (g) |
|---|---|
| Naloxone-Containing Composition A | |
| Naloxone HCl dihydrate | 1.199 |
| α-D-Lactose Monohydrate | 5.088 |
| Water for irrigation | 56.580 |
| Total | 62.867 |
| Naloxone-Containing Composition C | |
| Naloxone HCl dihydrate | 1.199 |
| α-D-Lactose Monohydrate | 4.469 |
| Kollidon 30 (BASF, Germany) | 0.619 |
| Water for irrigation | 56.580 |
| Total | 62.867 |
| Naloxone-Containing Composition D | |
| Naloxone HCl dihydrate | 2.398 |
| α-D-Lactose Monohydrate | 3.889 |
| Water for irrigation | 56.580 |
| Total | 62.867 |

Compositions A and C comprised single doses of naloxone of 4 mg, and Composition D comprised a single dose of naloxone of 8 mg (each calculated as the HCl salt). PSD and aPSD were analyzed using the general method in Example 4 above (see Table 6 below for results).

TABLE 6

| Composition | A | C | D |
|---|---|---|---|
| d10 (μm) | 15 | 17 | 17 |
| d90 (μm) | 44 | 57 | 58 |
| % <5 μm | 0 | 0 | 0 |

Example 6

Intranasally-Administered Naloxone—Pharmacokinetic Study (Healthy Volunteers)

A Phase I clinical study was performed to determine the bioavailability of the four investigational naloxone nasal powder formulations (obtained as described in Examples 4 and 5 above) relative to the reference commercial product NARCAN® nasal spray ('Ref'; naloxone hydrochloride liquid nasal spray, 4 mg; Adapt Pharma, Inc., Radnor, Pa., USA).

The study was a single-centre, open label, randomised, single dose 5-treatment crossover, relative bioavailability study in healthy subjects. Each subject received each of the four naloxone-containing powders (Compositions A to D), as well as Ref in a sequence according to a pre-set randomisation schedule, separated by a minimum 24 hours washout.

Subjects were randomised immediately before administration of the first dose of investigational medicinal product (IMP) or Ref (if used). A computer-generated randomisation schedule was used to allocate subject numbers to 1 of 10 treatment sequences (according to a balanced Williams design) with 2 subjects receiving each treatment sequence.

48 subjects were screened for inclusion in the study up to 28 days before dosing. 21 eligible subjects (healthy male and non-pregnant, non-lactating, female subjects between 18 and 55 years of age with a body mass index between 18.0 and 32.0 $kg/m^2$) were admitted to the clinical unit on the evening prior to IMP administration (Day −1) and remained on site until being discharge at 24 hours post-final dose (after receiving all 5 treatments).

Subjects received IMP or Ref in the morning of Days 1, 2, 3, 4 and 5, with an appropriate interval between subjects based on logistical requirements (approximately 10 minutes). IMP was administered to alternate nostrils on each day of dosing, starting with the left nostril on Day 1. A follow-up phone call took place 3 to 5 days after the final dose to ensure the ongoing wellbeing of the subjects.

Of the 21 subjects that were enrolled, all received IMP. For analysis purposes, all 21 subjects were included in the safety population, safety analysis dataset and the PK population. 1 profile was excluded from the PK analysis dataset owing to a dosing failure, such that 20 subjects completed the study and were included in the PK analysis dataset.

Plasma concentrations of naloxone were analysed using non-compartmental analysis methods to obtain estimates of standard PK parameters as set out below:

| Parameter | Definition |
| --- | --- |
| AUC(0-t) | area under the curve from 0 time to the last measurable concentration |
| AUC(0-inf) | area under the curve from 0 time extrapolated to infinity |
| AUCextrap | percentage of AUC(0-inf) extrapolated beyond the last measurable concentration |
| Cmax | maximum observed concentration |
| Tlag | Time to the first measurable concentration |
| Tmax | Time of maximum observed concentration |
| Lambda-z | slope of the apparent elimination phase |
| T1/2 | apparent elimination half-life |
| AUC(0-4 min) | area under the curve from 0 time to 4 min (0.067 h) post-dose |
| AUC(0-10 min) | area under the curve from 0 time to 10 min (0.17 h) post-dose |
| AUC(0-30 min) | area under the curve from 0 time to 30 min (0.5 h) post-dose |

The evaluation of safety parameters comprised analysis of adverse events (AEs), intranasal tolerability, laboratory evaluations, vital signs, electrocardiogram (ECG) and physical examination findings.

Log-transformed exposure parameters (AUCs and Cmax) were compared with standard methods to assess relative bioavailability using SAS Software procedure PROC MIXED. A single mixed effects model was fitted for each parameter to obtain estimates of geometric mean ratios (GMRs) and corresponding confidence intervals (CIs) for all treatment comparisons of interest. Models included terms for actual treatment received, study day (i.e. period) and planned sequence fitted as fixed effects and subject within sequence fitted as a random effect. Results were presented back-transformed to the linear scale. The following comparisons were of interest:

- Relative bioavailability compared to Ref: IMP:Ref GMRs for AUC(0-t), AUC(0-inf) and Cmax were determined
- Early exposure compared to Ref: IMP:Ref GMRs for AUC(0 0-4 min), AUC(0-10 min) and AUC(0-30 min) were determined
- Dose proportionality of IMD formulations: 8 mg:4 mg GMRs for AUC(0-t), AUC(0-inf) and Cmax were determined and dose normalized.

Results

Arithmetic mean naloxone plasma concentrations vs time, by treatment (linear scale) are shown in FIGS. 10 and 11 (first five hours and first hour after administration, respectively) and are described in Table 7 below. Geometric mean naloxone plasma concentrations vs time, by treatment (semi log scale) are described in Table 7 below.

TABLE 7

| Composition | A | B | C | D | Ref |
| --- | --- | --- | --- | --- | --- |
| N | 19 | 20 | 20 | 20 | 20 |
| AUC(0-t) (ng · h/mL)$^a$ | 10.7 (24.8) | 14.7 (18.5) | 10.9 (27.6) | 16.9 (35.9) | 7.99 (44.1) |
| AUC(0-inf) (ng · h/mL)$^a$ | 10.8 (25.3) [n = 18] | 14.8 (18.6) | 11.1 (28.7) [n = 18] | 17.1 (35.9) [n = 18] | 8.06 (44.6) [n = 19] |
| AUCextrap (%)$^a$ | 0.955 (50.5) [n = 18] | 0.688 (43.9) | 1.254 (79.7) [n = 18] | 0.865 (106.0) [n = 18] | 1.240 (58.0) [n = 19] |
| Cmax (ng/mL)$^a$ | 8.43 (44.2) | 15.6 (46.5) | 8.94 (35.4) | 12.1 (45.4) | 5.67 (55.8) |
| Tlag (h)$^b$ | 0.000 (0.00-0.033) | 0.000 (0.00-0.00) | 0.000 (0.00-0.034) | 0.000 (0.00-0.034) | 0.000 (0.00-0.035) |
| Tmax (h)$^b$ | 0.3333 (0.108-0.667) | 0.2500 (0.117-0.500) | 0.2500 (0.118-0.500) | 0.3333 (0.167-0.667) | 0.3333 (0.117-0.502) |
| Lambda-z | 0.59019 | 0.57066 | 0.53326 | 0.50483 | 0.52148 |

TABLE 7-continued

| Composition | A | B | C | D | Ref |
|---|---|---|---|---|---|
| (1/h)[c] | (20.9) [n = 18] | (20.6) | (31.7) [n = 18] | (20.0) [n = 18] | (24.7) [n = 19] |
| T1/2 | 1.243 | 1.269 | 1.471 | 1.425 | 1.404 |
| (h)[c] | (30.0) [n = 18] | (22.8) | (43.6) [n = 18] | (20.0) [n = 18] | (23.2) [n = 19] |

N: number of subjects in the dataset; n: number of subjects with an observation.
[a]Geometric mean (geometric CV %); [b]Median (range); [c]Arithmetic mean (arithmetic CV %)

The analysis of relative bioavailability (GMR, 90% CI) is shown in Table 8 below.

TABLE 8

| Comparison | AUC(0-t) (%) | AUC(0-inf) (%) | Cmax (%) |
|---|---|---|---|
| A:Ref | 136.23 | 135.47 | 149.56 |
|  | (122.64, 151.33) | (121.33, 151.26) | (125.75, 177.87) |
| B:Ref | 184.47 | 183.89 | 274.68 |
|  | (166.36, 204.55) | (165.28, 204.60) | (231.63, 325.74) |
| C:Ref | 136.37 | 136.91 | 157.57 |
|  | (122.99, 151.22) | (122.58, 152.92) | (132.88, 186.86) |
| D:Ref | 211.37 | 213.61 | 213.07 |
|  | (190.62, 234.38) | (191.25, 238.58) | (179.68, 252.67) |

All IMPs displayed significantly higher overall and peak plasma exposure of naloxone than Ref. Composition B displayed the highest relative bioavailability of the 4 mg formulations, with approximately 84% higher AUC and 175% higher Cmax than Ref on average (noting that formulation D included 8 mg naloxone hydrochloride, double the amount in the other formulations). The IMPs, A, B, C and D, also displayed lower interpatient variability (CV) in overall and peak exposure parameters than Ref (see Table 7).

Tables 9 and 10 below shows descriptive statistics of naloxone partial AUCs (as geometric means; geometric CV %) by treatment, on an absolute (Table 9) and relative (Table 10) basis.

TABLE 9

| Composition | A | B | C | D | Ref |
|---|---|---|---|---|---|
| AUC(0-4 min) | 0.0412 | 0.0895 | 0.0469 | 0.0543 | 0.0238 |
| (ng · h/mL)[a] | (149.1) | (175.4) | (159.6) | (262.7) | (186.5) |
| AUC(0-10 min) | 0.450 | 0.991 | 0.479 | 0.550 | 0.267 |
| (ng · h/mL)[a] | (90.7) | (87.8) | (90.2) | (104.9) | (103.7) |
| AUC(0-30 min) | 2.70 | 4.82 | 2.89 | 3.86 | 1.88 |
| (ng · h/mL)[a] | (46.1) | (42.9) | (43.6) | (52.3) | (60.8) |

TABLE 10

| Comparison | AUC(0-4 min) (%) | AUC(0-10 min) (%) | AUC(0-30 min) (%) | AUC(0-t) (%) |
|---|---|---|---|---|
| A:Ref | 174.56 | 167.04 | 144.29 | 136.23 |
|  | (109.45, 278.41) | (122.05, 228.59) | (120.63, 172.59) | (122.64, 151.33) |
| B:Ref | 376.43 | 370.69 | 256.89 | 184.47 |
|  | (237.87, 595.70) | (272.29, 504.64) | (215.41, 306.36) | (166.36, 204.55) |
| C:Ref | 197.03 | 179.25 | 153.80 | 136.37 |
|  | (124.51, 311.80) | (131.67, 244.03) | (128.96, 183.41) | (122.99, 151.22) |
| D:Ref | 228.33 | 205.89 | 205.54 | 211.37 |
|  | (144.28, 361.33) | (151.24, 280.30) | (172.35, 245.12) | (190.62, 234.38) |

All IMPs displayed significantly higher plasma exposure of naloxone than Ref over the first 4, 10 and 30 minutes after dosing. For Composition B, early partial AUC GMRs were much higher than the corresponding AUC(0-t) GMR for this IMP, which is indicative of a higher initial rate of absorption from this formulation than with Ref.

Analysis of dose proportionality of IMPs as dose normalised GMRs (90% CI; 8 mg:4 mg; D:A) are shown in Table 11 below.

TABLE 11

| Comparison | AUC(0-t) (%) | AUC(0-inf) (%) | Cmax (%) |
|---|---|---|---|
| D:A | 77.58 | 78.84 | 71.23 |
|  | (69.84, 86.17) | (70.46, 88.21) | (59.90, 84.72) |

For the scaled point estimates of D:A GMRs for AUC(0-t), AUC(0-inf) and Cmax, the 90% CIs lie entirely below 100%.

All IMPs demonstrated significantly higher naloxone exposure than Ref Compositions A, B, C and D displayed approximately 36%, 84%, 37% and 112% higher overall exposure, respectively, relative to Ref, with peak exposure (Cmax) being 50%, 175%, 58% and 113% higher on average, respectively (again noting that Composition D contained 8 mg naloxone hydrochloride, which is double the amount of the other compositions.)

Inter-subject variability in the overall exposure parameters AUC(0-t), AUC(0-inf) and Cmax was lower following administration of Compositions A, B, C and D compared to Ref.

As can be seen clearly from FIG. 10 and, more clearly from FIG. 11, rapid absorption of all formulations, with median Tmax values between 0.250 h and 0.333 h, was observed. Early exposure (in terms of AUC(0-4 min), AUC(0-10 min) and AUC(0-30 min)) was higher from all IMPs than that from Ref. Absorption was most rapid from Composition B, with point estimates indicative of >270% higher exposure than Ref during the first 10 min after dosing. This is a remarkable and completely unexpected result, for all of the reasons described hereinbefore.

Elimination of naloxone was similar between all formulations, with arithmetic mean terminal T1/2 values between 1.243 and 1.471 hours.

Nasal administration of naloxone nasal powder at all doses was considered to be safe and well tolerated under the conditions of the trial.

There were no SAEs, severe AEs or AEs leading to subject withdrawal reported in this study, and the AE profiles were similar to previous studies of the reference nasal spray in healthy subjects. The most commonly reported AEs were nasal inflammation, headache and dizziness. All AEs were mild in severity and, overall, the safety profile of the IMPs corresponded well with previous experience of naloxone HCl in healthy subjects and there were no findings that raised any safety concerns.

Example 7

Physical Stability of Spray-Dried Powders Containing Dextrins

The general procedure as described in Example 1 above was employed to make two formulations with the following compositions (percentages are by weight of the total composition):

Composition X

Naloxone HCl (35%), 2-hydroxypropyl-β-cyclodextrin (Cavasol W7, HP Pharma, Wacker, Germany; 53%), lactose (Merck, Germany; 10%) and Tween 20 (Croda Nordica AB, Sweden; 1%)

Composition Y

Naloxone HCl (17%), maltodextrin (Glucidex IT 12 DE, Roquette, France; 72%), lactose (10%), sucrose monolaurate (1%).

A similar experiment to that described in Example 2 above was set up measuring physical stabilities of Compositions X and Y at different RH values, as Tg values. The results are show in Table 12 below.

TABLE 12

| Composition | RH (%) | Tg (° C.) |
|---|---|---|
| X | Dried | 152 |
|   | 11 | 128/97 |
|   | 22 | 108/78 |
|   | 33 | 96/— |
|   | 43 | 81/52 |
| Y | Dried | 158/— |
|   | 11 | 156/97 |
|   | 22 | 142/85 |
|   | 33 | 128/70 |
|   | 43 | 107/51 |

Both dextrins increased Tg compared to compositions comprising only lactose as carrier material, facilitating acceptable emitted dose even after 24-72 hours of storage at 80° C. The multiple Tg values presented in Table 10 indicates that the relevant compositions were not fully homogenous, but rather regions with an increased concentration of higher molecular weight polysaccharide that are separate from regions of lower molecular weight compounds.

Subsequently-conducted dissolution tests also showed that high concentrations of maltodextrin did not affect the dissolution of naloxone.

Example 8

Chemical Stability of Spray-Dried Powders Containing Dextrins

In order to explore the chemical stability of naloxone as an effect of dextrins and lactose/dextrin mixtures, samples were prepared using the general procedure as described in Example 1 above. Compositions (percentages are by weight of the total composition) are provided in Table 13.

The chemical stability of naloxone after 3 and 6 months at 40° C./75% RH, with amounts of impurities expressed as a percentage of the related substance (% RS) is summarized for the different compositions in Table 13 below. All initial % RS values were less than 0.1%.

TABLE 13

| Composition | 3M | 6M |
|---|---|---|
| Naloxone HCl (17%) | 0.38 (0.10) | 0.07 (0.04) |
| Lactose (83%) | | |
| Naloxone HCl (17%) | 0.34 (0.09) | 0.19 (0.06) |
| Lactose (82%) | | |
| Sucrose monolaurate (1%) | | |
| Naloxone HCl (17%) | 0.75 (0.62) | 3.40 (3.40) |
| 2-hydroxypropyl-β-cyclodextrin (82%) | | |
| Sucrose monolaurate (1%) | | |
| Naloxone HCl (17%) | 0.09 (0.06) | 0.24 (0.21) |
| 2-hydroxypropyl-β-cyclodextrin (58%) | | |
| Lactose (24%) | | |
| Sucrose monolaurate (1%) | | |
| Naloxone HCl (35%) | 0.45 (0.42) | 3.05 (3.05) |
| 2-hydroxypropyl-β-cyclodextrin (64%) | | |
| Sucrose monolaurate (1%) | | |
| Naloxone HCl (35%) | 0.12 (0.09) | 0.71 (0.68) |
| 2-hydroxypropyl-β-cyclodextrin (45%) | | |
| Lactose (19%) | | |
| Sucrose monolaurate (1%) | | |
| Naloxone HCl (17%) | 0.39 (0.24) | 0.29 (0.29) |
| Maltodextrin 12DE (82%) | | |
| Sucrose monolaurate (1%) | | |
| Naloxone HCl (17%) | 0.12 (0.05) | 0.05 (0.05) |
| Maltodextrin 12DE (63%) | | |
| Lactose (19%) | | |
| Sucrose monolaurate (1%) | | |
| Naloxone HCl (35%) | 0.29 (0.29) | 0.28 (0.28) |
| Maltodextrin 12DE (64%) | | |
| Sucrose monolaurate (1%) | | |
| Naloxone HCl (35%) | 0.13 (0.10) | 0.11 (0.08) |
| Maltodextrin 12DE (45%) | | |
| Lactose (19%) | | |
| Sucrose monolaurate (1%) | | |

The numbers in brackets in Table 13 are the % RS taking away that value measured for Impurity E (Imp E), which is a documented impurity related to naloxone (dimer). In this study, Imp E seems to be formed during sample preparation prior to analysis, which affects the total % RS value in an uncontrolled way and prevents the detection of minor degradation trends.

It is clear from Table 13 that dextrins unexpectedly induce decomposition of naloxone, but that the addition of lactose mitigates this effect.

Example 9

Nalmefene-Containing Compositions E, F and G

The same general procedure essentially as described in Examples 1 and/or 4 above was followed to prepare three nalmefene-containing spray-dried powders, with compositions according to Table 14 below. In this and the next example, nalmefene was sourced from Mallinckrodt Inc., USA.

TABLE 14

| Component | Quantity per batch (g) |
|---|---|
| Nalmefene-Containing Composition E | |
| Nalmefene HCl | 3.106 |
| α-D-Lactose Monohydrate | 18.162 |

TABLE 14-continued

| Component | Quantity per batch (g) |
|---|---|
| Sucrose monolaurate | 0.206 |
| Water for irrigation | 193.257 |
| Total | 214.731 |
| Nalmefene-Containing Composition F | |
| Nalmefene HCl | 3.004 |
| α-D-Lactose Monohydrate | 4.188 |
| Maltodextrin 12DE | 12.713 |
| Sucrose monolaurate | 0.199 |
| Water for irrigation | 178.852 |
| Total | 198.956 |
| Nalmefene-Containing Composition G | |
| Nalmefene HCl | 3.284 |
| α-D-Lactose Monohydrate | 9.158 |
| Maltodextrin 12DE | 31.298 |
| Sucrose monolaurate | 0.218 |
| Water for irrigation | 395.620 |
| Total | 439.578 |

Compositions E and F comprised single doses of nalmefene of 3 mg, and Composition G comprised a single dose of nalmefene of 3 mg, but at half concentration and double fill weight (each calculated as the free base). PSD and aPSD were analyzed using the general method in Example 4 above (see Table 15 below for results).

TABLE 15

| Composition | E | F | G |
|---|---|---|---|
| d10 (μm) | 18 | 20 | 19 |
| d90 (μm) | 51 | 66 | 65 |
| % <5 μm | 0 | 0 | 0 |

Using the method described in Example 2 above, all of the compositions exhibited a glass transition at around 60° C., in ambient conditions. However, Composition E produced a large crystallisation event at just above 100° C., which was not seen in the maltodextrin-containing Compositions F and G. In addition, Composition E underwent crystallization at room temperature in 60% RH, something that was not seen in Compositions F and G.

Example 10

Chemical Stability of Spray-Dried Powders Containing Nalmefene

Samples were prepared using the general procedure essentially as described in Examples 1 and/or 4 above. Compositions (percentages are by weight of the total composition) are provided in Table 16 below.

The chemical stability of nalmefene 3 and 6 months at 40° C./75% RH, with amounts of impurities expressed as a percentage of the related substance (% RS) is summarized for the different compositions in Table 16 below. All initial % RS values were less than 0.1%.

TABLE 16

| Composition | 3M | 6M |
|---|---|---|
| Nalmefene HCl (15%, 0.45 g) Lactose (84%) Sucrose monolaurate (1%) | 0.14 | 0.05 |

TABLE 16-continued

| Composition | 3M | 6M |
|---|---|---|
| Nalmefene HCl (15%, 0.45 g) Maltodextrin 12DE (64%) Lactose (20%) Sucrose monolaurate (1%) | 0.10 | 0.00 |
| Nalmefene HCl (15%, 0.45 g) Maltodextrin 12DE (74%) Lactose (10%) Sucrose monolaurate (1%) | 0.11 | 0.07 |
| Nalmefene HCl (7.5%, 0.225 g) Maltodextrin 12DE (71.5%) Lactose (20%) Sucrose monolaurate (1%) | 0.16 | 0.00 |

The invention claimed is:

1. A solid pharmaceutical composition in the form of a spray-dried powder that is suitable for nasal delivery of naloxone or a pharmaceutically acceptable salt thereof, to treat opioid overdose, comprising:
   a pharmacologically-effective amount of naloxone or a pharmaceutically acceptable salt thereof; and
   a pharmaceutically-acceptable carrier material comprising a combination of:
   (i) a disaccharide selected from the group consisting of maltitol, trehalose, sucralose, sucrose, isomalt, maltose, and lactose; and
   (ii) a dextrin;
   wherein the naloxone or pharmaceutically acceptable salt thereof is less than about 15% chemically degraded after 3 months at 75% relative humidity and 40° C.

2. A composition as claimed in claim 1, wherein the powder has a particle size distribution that includes a d10 that is above about 3 μm.

3. A composition as claimed in claim 1, wherein the disaccharide comprises lactose and/or trehalose.

4. A composition as claimed in claim 1, wherein the dextrin comprises a cyclodextrin or a maltodextrin.

5. A composition as claimed in claim 1, wherein the carrier material comprises α-D-lactose monohydrate as the lactose disaccharide and one or both of 2-hydroxypropyl-β-cyclodextrin and maltodextrin 12DE as the dextrin.

6. A composition as claimed in claim 1, wherein the disaccharide is present in an amount of between about 10% and about 30% by weight based on the total weight of the composition.

7. A composition as claimed in claim 1, wherein the dextrin is present in an amount of between 40% and about 80% by weight based on the total weight of the composition.

8. A composition as claimed in claim 1, wherein the lowest measurable glass transition temperature of the composition is at least about 40° C. when measured at a relative humidity of up to about 35%.

9. A composition as claimed in claim 1, wherein the powder has a particle size distribution that includes a volume-based mean diameter within the range of about 10 μm and about 100 μm.

10. A process for the manufacturing of a composition as defined in claim 1, wherein said process comprises the steps of:
   i) mixing together naloxone or salt thereof, the pharmaceutically-acceptable carrier materials in an appropriate volatile solvent; and
   ii) spray-drying the mixture from step i) to form a spray-dried plurality of particles.

11. A composition obtainable by a process as defined in claim 10.

12. A nasal applicator device suitable and/or adapted for delivery of a composition as defined in claim 1 to the nose, which comprises, or is adjunct and/or attached to, a reservoir, within which reservoir said composition is contained.

13. A process for the manufacturing of an applicator device as claimed in claim 12, the process comprising:
   i) mixing together naloxone or salt thereof and the pharmaceutically-acceptable carrier materials in an appropriate volatile solvent;
   ii) spray-drying the mixture from step i) to form a spray-dried plurality of particles; and
   iii) loading the composition formed in step ii) into the reservoir within or adjunct or attached to said applicator device.

14. A method of treating opioid overdose, which method comprises administering a composition as defined in claim 1 to a subject in need of such treatment.

15. A method as claimed in claim 14, wherein the composition is administered to said subject by way of an applicator that comprises or is adjunct and/or attached to, a reservoir, within which reservoir said composition is contained.

* * * * *